(12) United States Patent
Odland

(10) Patent No.: US 6,942,634 B2
(45) Date of Patent: Sep. 13, 2005

(54) SYSTEM FOR TREATING TISSUE SWELLING

(75) Inventor: Rick Mathew Odland, Roseville, MN (US)

(73) Assignee: Twin Star Medical, Inc., Minneapolis, MN (US)

(*) Notice: Subject to any disclaimer, the term of this patent is extended or adjusted under 35 U.S.C. 154(b) by 0 days.

(21) Appl. No.: 10/273,376

(22) Filed: Oct. 17, 2002

(65) Prior Publication Data

US 2003/0187367 A1 Oct. 2, 2003

Related U.S. Application Data

(63) Continuation-in-part of application No. 10/104,113, filed on Mar. 22, 2002.

(51) Int. Cl.[7] .......................... A61M 37/00; C02F 1/44
(52) U.S. Cl. ..................................... 604/6.09; 210/650
(58) Field of Search ................................ 604/4.01, 601, 604/5.01–5.04, 6.07, 6.11, 6.16, 19, 27–8, 30, 23–4, 48, 500, 503–508, 65; 73/863, 863.21, 863.31, 863.71, 863.81; 128/898; 435/1.1, 1.2; 210/645, 650–52, 739, 762, 790, 85, 90, 194, 195.1–195.2, 252–3, 255, 257.1–257.2, 258–260, 321.6, 321.65, 321.71–321.72, 321.78–321.79, 321.8, 322, 323.1–323.2, 500.1, 348, 500.21, 500.23

(56) References Cited

U.S. PATENT DOCUMENTS

| | | | |
|---|---|---|---|
| 3,619,423 A | * 11/1971 | Galletti et al. ............... | 210/632 |
| 4,235,231 A | 11/1980 | Schindler et al. ........... | 128/214 |
| 4,274,417 A | 6/1981 | Delpy ......................... | 128/632 |
| 4,340,615 A | 7/1982 | Goodwin et al. ............... | 427/2 |
| 4,647,378 A | 3/1987 | Minami ...................... | 210/646 |
| 4,726,381 A | 2/1988 | Jones ......................... | 128/632 |
| 5,336,164 A | 8/1994 | Snider et al. .................. | 604/4 |
| 5,441,481 A | 8/1995 | Mishra et al. ................ | 604/29 |
| 5,484,399 A | 1/1996 | DiResta et al. ............... | 604/21 |
| 5,501,663 A | 3/1996 | Hattler et al. ................ | 604/26 |
| 5,730,712 A | * 3/1998 | Falkvall et al. ............ | 604/5.01 |
| 5,865,789 A | 2/1999 | Hattler ........................ | 604/26 |
| 6,030,358 A | * 2/2000 | Odland ....................... | 604/27 |
| 6,287,608 B1 | 9/2001 | Levin et al. ................ | 424/718 |
| 2003/0181824 A1 | * 9/2003 | Odland ....................... | 600/573 |

FOREIGN PATENT DOCUMENTS

| | | |
|---|---|---|
| WO | PCT/US98/16416 | 2/1999 |
| WO | WO 02/36068 | 5/2002 |
| WO | WO 02/47609 | 6/2002 |
| WO | WO 02/053098 | 7/2002 |

OTHER PUBLICATIONS

University of Wisconsin press release dated Dec. 12, 2001, "Novel Device Takes Over Where Medicinal Leeches Leave Off" (http://www.sciencedaily.com/releases/2001/12/011213084919.htm).

* cited by examiner

Primary Examiner—Patricia Bianco
(74) Attorney, Agent, or Firm—Fredrikson & Byron, P.A.

(57) ABSTRACT

A system and related methods and components for treating tissue swelling, and particularly swelling associated with cerebral edema, compartment syndrome, and congestive heart failure, by the use of water removal therapy, in order to remove only water from biological fluids. Included also is a system for such use that incorporates one or more monitors, optionally in addition to the use of water removal therapy. By removing only water, all other biologic agents, including essentially all solutes and formed blood elements (such as cells) are increased in concentration in the remaining bodily fluid(s). WRT can be applied to several clinical conditions in which there is an excess of water, and is ideally used in an extracorporeal fashion, in combination with other functions and related components as well, including ultrafiltration.

42 Claims, 22 Drawing Sheets

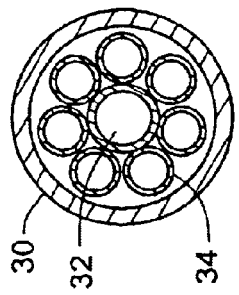
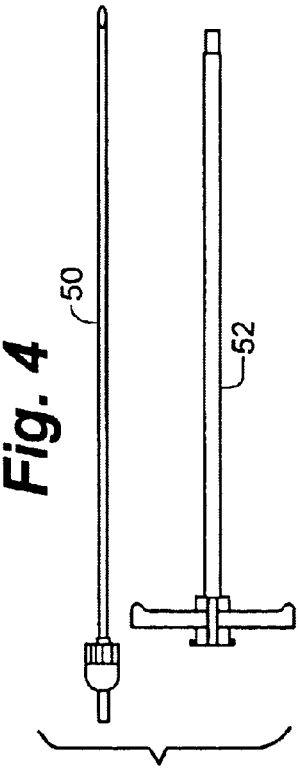
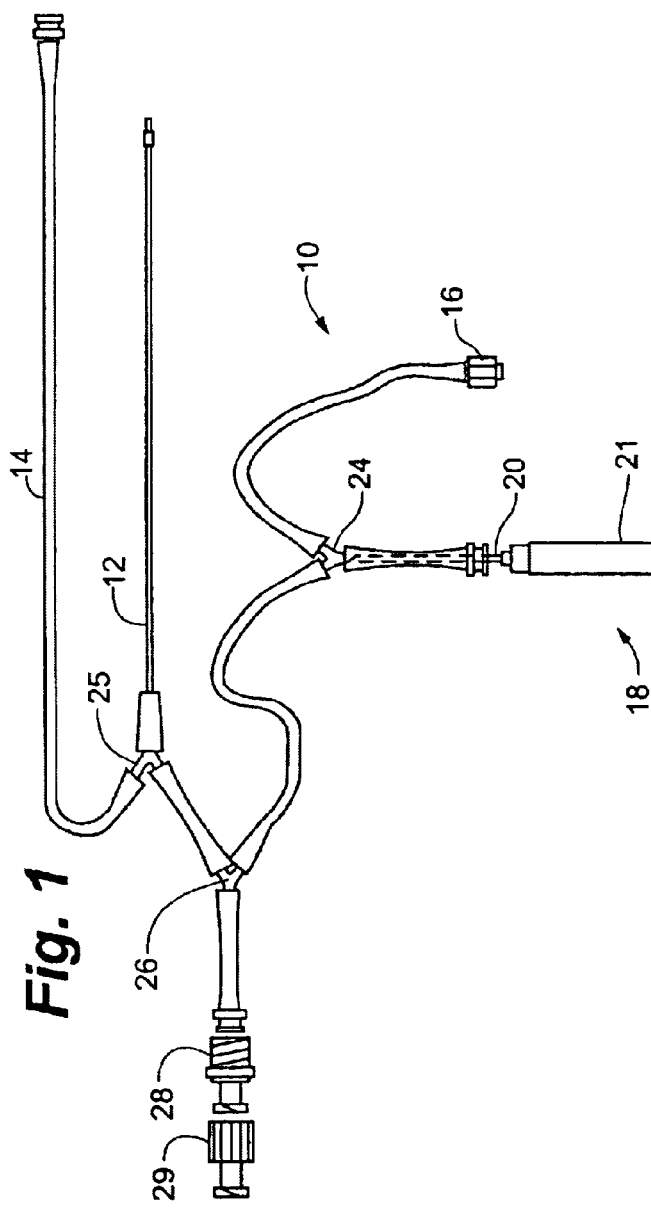
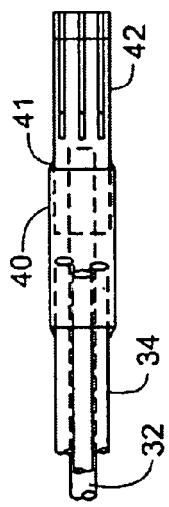

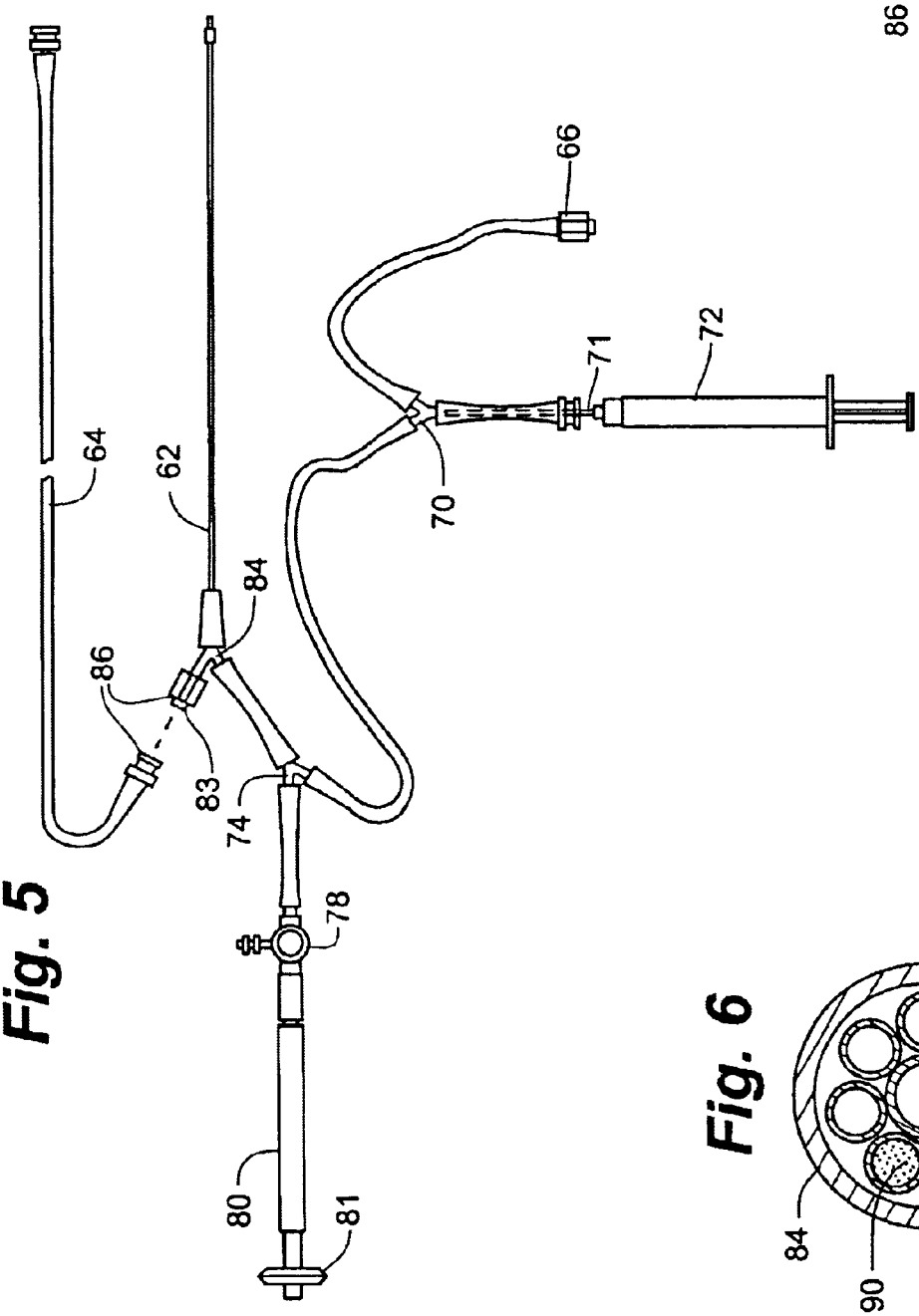

Fig. 28

| SOURCE | MATERIAL | PORE SIZE (EXPRESSED IN KILODALTONS (KD) OR MICRONS) | ID (MM) | OD (MM) |
|---|---|---|---|---|
| A/G TECHNOLOGY CORP. NEEDHAM, MA | POLYSULFONE | 10KD | 0.25, 0.5, 1 | 0.5, 1, 1.8 |
|  | POLYSULFONE | 30KD | 0.5, 1, 2, 3 | 1, 1.8, 3, 4 |
|  | POLYSULFONE | 50KD | 0.5, 1 | 1, 1.8 |
|  | POLYSULFONE | 0.1μm | 0.75, 1, 2 | 1.5, 1.8, 3 |
|  | POLYSULFONE | 0.2μm | 1 | 1.8 |
|  | POLYSULFONE | 0.45μm | 1 | 1.8 |
| AKZO NOBEL | CELLULOSE | 10KD | 0.2 | 0.216 |
| ASAHI | POLYACRYLONITRILE (PAN) | 50KD | 0.25 | 0.32 |
| CORSEP | PAN | 50KD | 0.2 | 0.31 |
|  | POLYETHER-SULFONE | 0.1μm | 0.6 | 1.0 |
|  | POLYETHER-SULFONE | 0.2μm | 0.6 | 1.0 |
|  | POLYETHER-SULFONE | 0.5μm | 0.6 | 1.0 |
| MINNTECH (MINNEAPOLIS, MN) | POLYETHER-SULFONE | 10KD | 0.2 | 0.28 |
|  | POLYETHER-SULFONE | 30KD | 0.28 | 0.36 |
|  |  | 70KD | 0.2 | 0.28 |
|  | POLYETHER-SULFONE | 0.05μm | 0.28 | 0.36 |
|  | POLYETHER-SULFONE | 0.2μm | 0.28 | 0.36 |
|  | POLYETHER-SULFONE | 0.45μm | 0.28 | 0.36 |
| SPECTRUM LABORATORIES (RANCHO DOMINQUEZ, CA) | POLYETHER-SULFONE | 0.2μm | 0.5, 1.0 | 0.9, 1.4 |
|  | CELLULOSE | 0.1μm | 0.64 | 0.86 |
|  | CELLULOSE | 0.2μm | 0.64, 1 | 0.86, 1.2 |

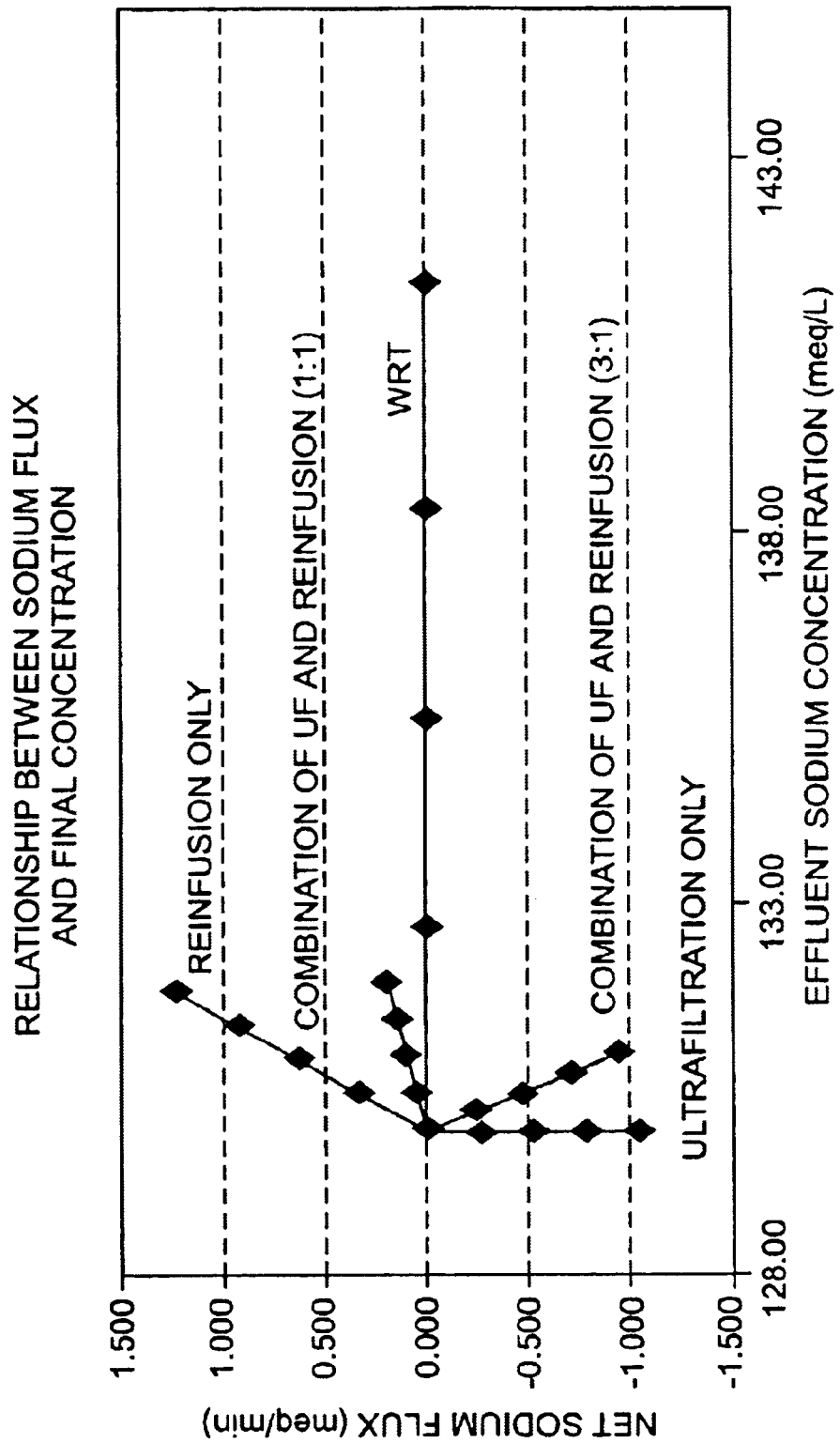

Fig. 31a

| PROCESS(ES) | INSIDE | OUTSIDE | ADVANTAGES |
|---|---|---|---|
| WRT | GAS | BLOOD | MAXIMAL CONCENTRATION OF ALL SPECIES. HIGHER GAS VELOCITY POSSIBLE, DEPENDING ON DESIGN |
| WRT | BLOOD | GAS | MAXIMAL CONCENTRATION OF ALL SPECIES. |
| WRT | | BLOOD | FOR REMOVAL OF KETONES, AMMONIA, OTHER VAPORS USING SOLUBLE MEDIA, INCLUDING GAS OR LIQUIDS |
| WRT UF | BLOOD/GAS | GAS/BLOOD | COMBINATION OF SALT REMOVAL AND CONCENTRATION |
| WRT UF HD | BLOOD/GAS | GAS/BLOOD | COMBINATION WITH MAXIMAL OPTIONS. |
| WRT UF HD RI | BLOOD/GAS | GAS/BLOOD | COMBINATION WITH MAXIMAL OPTIONS. |
| WRT UF RI | BLOOD/GAS | GAS/BLOOD | COMBINATION WITH MAXIMAL OPTIONS. |
| WRT UF RI HD | BLOOD/GAS | GAS/BLOOD | COMBINATION WITH MAXIMAL OPTIONS. |
| WRT HD | BLOOD/GAS | GAS/BLOOD | WILL IMPROVE DIALYSIS EXCHANGE BY INCREASING CONCENTRATION |
| WRT HD RI | BLOOD/GAS | GAS/BLOOD | IMPROVED EXCHANGE, WITH MAXIMAL OPTIONS. |
| WRT HD RI UF | BLOOD/GAS | GAS/BLOOD | IMPROVED EXCHANGE, WITH MAXIMAL OPTIONS. |
| WRT HD UF | BLOOD/GAS | GAS/BLOOD | IMPROVED EXCHANGE, WITH MAXIMAL OPTIONS. |
| WRT HD UF RI | BLOOD/GAS | GAS/BLOOD | IMPROVED EXCHANGE, WITH MAXIMAL OPTIONS. |
| WRT RI | BLOOD/GAS | GAS/BLOOD | FURTHER OPTIONS FOR SPECIFIC CONCENTRATIONS. |

Fig. 31b

| PROCESS(ES) | INSIDE | OUTSIDE | ADVANTAGES |
|---|---|---|---|
| WRT RI UF | BLOOD/GAS | GAS/BLOOD | FURTHER OPTIONS FOR SPECIFIC CONCENTRATIONS. |
| WRT RI UF HD | BLOOD/GAS | GAS/BLOOD | FURTHER OPTIONS FOR SPECIFIC CONCENTRATIONS. |
| WRT RI HD | BLOOD/GAS | GAS/BLOOD | FURTHER OPTIONS FOR SPECIFIC CONCENTRATIONS. |
| WRT RI HD UF | BLOOD/GAS | GAS/BLOOD | FURTHER OPTIONS FOR SPECIFIC CONCENTRATIONS. |
| UF | BLOOD | ULTRAFILTRATE | RETAINS MOLECULES GREATER THAN MWCO. NO CONCENTRATION |
| UF HD | | | |
| UF HD RI | | | |
| UF HD RI WRT | | | |
| UF HD WRT | | | |
| UF HD WRT RI | | | |
| UF RI | | | |
| UF RI WRT | | | |
| UF RI WRT HD | | | |
| UF RI HD | | | |
| UF RI HD WRT | | | |
| UF WRT SERIES | | | |
| UF WRT PARALLEL | | | |

Fig. 31c

| PROCESS(ES) | INSIDE | OUTSIDE | ADVANTAGES |
|---|---|---|---|
| UF WRT STEPPED | | | |
| UF WRT STEPPED | | | |
| UF WRT COUNTERFLOW | | | |
| UF WRT HD | | | |
| UF WRT HD RI | | | |
| UF WRT RI | | | |
| UF WRT RI HD | | | |
| HD | | | DIFFUSIONAL EXCHANGE ONLY, BY CONCENTRATION GRADIENT |
| HD RI | | | IMPROVED VISCOSITY FOR WRT |
| HD RI WRT | | | IMPROVED VISCOSITY FOR WRT |
| HD RI WRT UF | | | |
| HD RI UF | | | IMPROVED VISCOSITY FOR WRT |
| HD RI UF WRT | | | FURTHER OPTIONS |
| HD WRT | | | FURTHER OPTIONS |
| HD WRT UF | | | FURTHER OPTIONS |
| HD WRT UF RI | | | FURTHER OPTIONS |
| HD WRT RI | | | FURTHER OPTIONS |
| HD WRT RI UF | | | |
| HD UF | | | |
| HD UF RI | | | |
| HD UF RI WRT | | | |

Fig. 31d

| PROCESS(ES) | INSIDE | OUTSIDE | ADVANTAGES |
|---|---|---|---|
| HD UF WRT | | | |
| HD UF WRT RI | | | |
| RI | | | NO HOLLOW FIBERS INVOLVED. SIMPLY GIVING INTRAVENOUS FLUID |
| RI HD | | | |
| RI HD UF | | | |
| RI HD UF WRT | | | IMPROVED VISCOSITY FOR EVENTUAL WRT |
| RI HD WRT | | | IMPROVED VISCOSITY FOR EVENTUAL WRT |
| RI HD WRT UF | | | IMPROVED VISCOSITY FOR EVENTUAL WRT |
| RI UF | | | |
| RI UF WRT | | | IMPROVED VISCOSITY FOR EVENTUAL WRT |
| RI UF WRT HD | | | IMPROVED VISCOSITY FOR EVENTUAL WRT |
| RI UF HD | | | |
| RI UF HD WRT | | | IMPROVED VISCOSITY FOR EVENTUAL WRT |
| RI WRT | | | IMPROVED VISCOSITY FOR EVENTUAL WRT |
| RI WRT HD | | | IMPROVED VISCOSITY, WITH POTENTIAL FOR HIGH EXCHANGE RATES WITHOUT NET FLUID REMOVAL. |
| RI WRT HD UF | | | IMPROVED VISCOSITY, WITH POTENTIAL FOR HIGH EXCHANGE RATES WITHOUT NET FLUID REMOVAL. |
| RI WRT UF | | | IMPROVED VISCOSITY, WITH POTENTIAL FOR HIGH EXCHANGE RATES WITHOUT NET FLUID REMOVAL. |
| RI WRT UF HD | | | IMPROVED VISCOSITY, WITH POTENTIAL FOR HIGH EXCHANGE RATES WITHOUT NET FLUID REMOVAL. |

SYSTEM FOR TREATING TISSUE SWELLING

CROSS REFERENCE TO RELATED APPLICATIONS

The present application is a continuation-in-part of U.S. patent application filed Mar. 22, 2002 and assigned Ser. No. 10/104,113, the entire disclosure of which is incorporated herein by reference.

FIELD OF THE INVENTION

The present invention relates to methods and apparatuses for use in treating tissue swelling, including cerebral edema, compartment syndrome and congestive heart failure. In another aspect, the invention relates to diagnostic and therapeutic methods and apparatuses that include the placement of semipermeable catheters and membranes within the body. In yet another aspect, the invention relates to diagnostic and therapeutic methods and apparatuses adapted to monitor various physiologic parameters in the course of tissue swelling, as well as methods and apparatuses adapted to deliver media, including gases and liquids, to catheters positioned within a tissue, including to treat biological (e.g., bodily) fluids external to the body. In a final aspect, the invention relates to systems, and components thereof, for recovering fluids from sites of tissue swelling.

BACKGROUND OF THE INVENTION

A number of clinical conditions involve (e.g., are caused by and/or themselves cause) impaired circulation, and particularly circulation within interstitial spaces and within discrete, localized tissues. Among the more vexing examples of such circulatory afflictions are those that involve localized tissue swelling, including compartment syndrome and edema (and in particular, cerebral edema).

Acute compartment syndrome generally involves impaired circulation within an enclosed fascial space (e.g., the anterior compartment of the lower leg), leading to increased tissue pressure and necrosis of muscle and nerves. The soft tissue of the lower leg is contained within four compartments, each bounded by heavy fascia—the anterior, lateral, superficial posterior, and deep posterior compartments. Once diagnosed, the injury requires immediate decompression through surgical release of the skin and fascia covering the area. Other proposed treatment strategies include the use of a sympathetic blockade, hyperbaric oxygen therapy, and treatment with mannitol and/or alloperinol.

Cerebral edema (also known as brain swelling), includes vasogenic cerebral edema (the most common form of edema) which manifests itself in the form of increased permeability of small vessels (breakdown of blood-brain barrier) and the escape of proteins and fluids into extracellular space, especially of white matter. Cerebral edema can be caused by ischemia, loss of oxygen, or focal disruption or loss of blood supply such as stroke. The diagnosis of cerebral edema is based on changes in mental status, imaging, and measurement of intracranial pressure. There remain few conventional treatment options, and they tend to be of limited efficacy.

Monitoring of intracranial pressure (ICP) is considered appropriate for all patients with severe traumatic brain injury (TBI). While the placement of an ICP monitor is invasive, the benefits of ICP monitoring are felt to offset this factor, carry a relatively small risk of complications (e.g., infection, hemorrhage, malfunction, obstruction or malposition), and rarely result in increased patient morbidity. Percutaneous devices (e.g., ventriculostomy catheters) for use in monitoring ICP are commercially available in a variety of styles and from a number of sources. Such devices are commonly placed within the cerebral ventricles, where they enable accurate and reliable monitoring of ventricular pressure and can be used for the therapeutic convective drainage of cerebrospinal fluid ("CSF").CSF drainage has been described as a potentially effective method of lowering ICP, particularly when ventricular size has not been compromised. CSF drainage typically requires penetration of the brain parenchyma with a ventricular catheter. A variety of ventricular catheters are available for such purposes, e.g., the "MoniTorr" product available from Integra Lifesciences, Inc. As fluid is removed, however, brain swelling often progresses to the point where the ventricular system is compressed and the ability to drain CSF can be compromised. This may be exacerbated by overdrainage, leading to the ventricular walls or the choroid plexus actually collapsing in a manner that occludes the orifices of the catheter. The therapeutic efficacy of convective CSF drainage by conventional ventriculostomy catheters, therefore, has been limited to date.

On a separate subject, gases have long been used for various medical procedures. For instance, oxygen is generally used to enriched the atmosphere for patient therapy and procedures, though oxygen is considered a drug and is dispensed by prescription. High-pressure oxygen is used for hyperbaric treatment, while in other situations, medical air is inhaled by patients, often through secondary pneumatic equipment. Nitrous oxide provides the first and second stages of anesthesia, while nitrogen itself powers pneumatic surgical tools. Carbon dioxide gas is becoming more common in piped systems as it gains more use in advanced respiratory treatment and operating room procedures. Also helium, and mixtures of helium with oxygen, have been described for the treatment of patients having certain respiratory conditions.

An assortment of references also describe either the delivery or recovery of media, such as gases or hyperosmolar liquids, for various purposes and into various locations within the body. Such references include, for instance, situations in which oxygen is delivered to the body by means of catheters positioned within the blood, as well as those in which gases are themselves measured within bodily fluids. See, e.g., U.S. Pat. No. 4,274,417 (Instruments for use in the measurement of gases in body fluids); U.S. Pat. No. 4,726,381 (Dialysis system and method); U.S. Pat. No. 4,340,615 (Apparatus for analysis of absorbed gases); U.S. Pat. No. 5,865,789 (Percutaneous oxygenator for inducing a retrograde perfusion of oxygenated blood); U.S. Pat. No. 5,336,164 (Intravascular membrane lung apparatus); and U.S. Pat. No. 5,501,663 (Inflatable percutaneous oxygenator with transverse hollow fibers).

See also Levin, et al. U.S. Pat. No. 6,287,608, which describes a method and apparatus for the treatment of congestive heart failure by improving perfusion of the kidney by infusion of a vasodilator.

On yet another subject, medical-surgical vacuum and drainage systems exist in the art as well. For instance, the American Society for Testing and Materials provides standard specifications (F960-86(2000)) for medical and surgical suction and drainage systems that include applications such as oral, nasal and tracheal suction, gastrointestinal drainage, pleural space and mediastinal drainage, and closed wound drainage. Other examples, though not included within this specification, can include drainage by the use of catheters and similar instruments inserted into tissue sites, syringes, breast pumps, dentistry suction, and waste gas scavenging. See, for instance, the Mini VAC (Vacuum Assisted Closure) device, available from KCI (San Antonio, Tex.). The VAC device provides negative pressure therapy for the treatment of chronic and acute wound, and allows for the measurement and monitoring of therapy at the wound site through micro-processor control and multi-lumen tubing. In use, the negative pressure is applied to a special dressing positioned in a wound cavity or over a flap or graft. The pressure distributing wound dressing, in turn, is said to help remove fluids from the wound.

In a more recent approach, a "mechanical leech" has been developed, with the intent of attaching to a wound site in order to remove blood and promote wound heeling. See, for instance, the University of Wisconsin press release dated Dec. 12, 2001, "Novel Device Takes Over Where Medicinal Leeches Leave Off".

See also U.S. Pat. No. 5,484,399, which describes a method and apparatus for reducing interstitial fluid pressure in tissues, particularly in tumors, by applying suction to the interior of the tissue. The method comprises inserting into the tissue one or more needle-like, elongated tubes, each having at least one hole at or near the end that is inserted into the tissue and each having means to apply suction to the protruding end. Components may be provided to measure the pressure within the tissue and to use this measurement to control the suction applied to the tissue through the tubes.

A variety of references describe the placement and use of semipermeable membranes within the body. See, for instance, Mishra (U.S. Pat. No. 5,441,481) which describes a microdialysis probe arranged to have a primary (e.g., electrical) probe secured to it to enable both the microdialysis and primary probe to be extended as a unit for selective sampling and/or administration of compounds to the body. The microdialysis probes are quite large, said to be on the order of 3–4 mm in diameter. Although the reference makes passing reference of the possible "therapeutic application" of their probe, e.g., at column 9, lines 6–20, the suggested delivery of a viscous dextran solution would seem to require the application of tremendous pressures. Moreover, the passage of water through the semipermeable membrane is taught as occurring via chemical (osmotic) means, as compared to water passage brought about by mechanical means, as the result of hydrostatic forces.

Applicant has also previously described methods and related systems for use in site specific therapy of a tissue site. See issued U.S. Pat. No. 6,030,358 and published PCT application No. PCT/US98/16416, the disclosures of which are incorporated herein by reference. In one embodiment, the PCT application provides a system that comprises one or more catheters adapted to be positioned within the tissue site and a delivery/recovery mechanism for employing the catheter(s) to control the movement of bulk fluids and/or active fluid components within or between tissue portions or adjacent tissues in a manner that achieves a therapeutic effect. The catheter(s), in turn, can comprise one or more semipermeable microcatheters, adapted to effect the movement of fluid or fluid components within the tissue site by microdialysis within the tissue site. In its various embodiments, the system previously described by Applicant can be used for the treatment of a variety of disorders, including cerebral edema and compartment syndrome.

In yet another embodiment, Applicant's PCT application describes an apparatus for performing site specific therapy in the event of cerebral edema, the apparatus comprising one or more catheters, each comprising one or more semipermeable membranes, adapted to be positioned in the parenchymal portion of the brain, and adapted to be flowably connected to a source of negative pressure sufficient to remove fluid from the brain in order to alleviate intracranial pressure.

While the embodiments of Applicant's US patent and PCT application remain viable, and valuable, options for various applications, it has become clear that continued efforts, and alternative approaches, are in order with respect to the treatment of tissue swelling, and particularly cerebral edema, as well as compartment syndrome.

Congestive Heart Failure

Congestive heart failure (CHF) provides yet another example of tissue swelling, and particularly nonlocalized tissue swelling. CHF involves the diminished capacity of the heart to circulate blood as a result of injury. The low blood pressure triggers mechanisms to retain body water causing fluid overload or tissue swelling. If CHF is severe, blood flow to the kidneys is restricted such that renal function is impaired without treatment. Over 5 million US patients have CHF with 500,000 newly diagnosed patients each year. Diuretic drugs are currently the primary treatment for CHF patients, but many patients become resistant to further diuretic drug therapy. This resistance leads to fluid overload and a diminished quality of life. Severe fluid overload often leads to hospitalization and more intensive medical therapy. There are about 1 million CHF related hospitalizations each year, typically lasting 4 days, costing an average of $15,000 per hospitalization for a total annual cost of $15 billion.

In addition to the tissue swelling that occurs during CHF, the failing heart is not able to maintain perfusion to vital organs. The body senses low perfusion as a loss of blood volume, and initiates mechanisms designed to retain body water. Sodium is retained as one method to prevent renal excretion of water. Overall, more water than sodium is retained, and hence, serum sodium concentrations are typically low. This, in turn, stimulates additional measures to retain sodium. With increasing water and sodium retention, the venous system becomes overfilled, resulting in an increase in interstitial fluid, and the resulting clinical symptoms of CHF. Excess interstitial fluid results in pulmonary edema, pitting edema of the lower limbs, sacral edema, and ascites. Failure to respond to medicines completes the clinical picture of refractory CHF. These patients must be admitted to the hospital for treatment.

CHF patients often present with low sodium, low potassium, and low magnesium levels. Patients who are hospitalized with chronic CHF have a 32–40% incidence of serum sodium less than 135 mmol/l. Low sodium levels are a problem for several reasons, including:

1) Poor response to drug treatment. Loop diuretics require sodium to be effective. Patients with low sodium become refractory to medical treatment and require hospitalization.

2) Longer length of stay.

3) Increased risk of inpatient death.

4) Increased risk of mortality after discharge.

Several new therapies have emerged to manage late stage CHF, particularly in patients that have become refractory to diuretic drug therapy. These new therapies include hemofiltration, ventricular assist devices, and sophisticated combination drug therapies. These therapies, including hemofiltration, have not only been shown to treat fluid overload, but have also demonstrated the potential reversibility of CHF. None of the emerging therapies address the problem of hyponatremia (low sodium) however, and some can actually tend to aggravate the problem.

Efforts to employ ultrafiltration technology in CHF, to date, have focused on using hemofiltration-like systems to treat CHF fluid overload. Such systems, like conventional hemofiltration used to treat renal failure (kidney dialysis therapy), can remove up to 4 liters in an 8-hour period. The ultrafiltrate is removed from the blood, which results in decreased blood volume and subsequent refilling of plasma fluid from the interstitial space. With ultrafiltration, only molecules less than the molecular weight cutoff of the membrane (generally about 50,000 Daltons) are removed with the water component of the blood. Since most proteins are not removed, ultrafiltration tends to cause a slight increase in colloid osmotic pressure, which can aid refilling of the intravascular space.

Ultrafiltration does not, however, improve serum sodium levels. To the contrary, small molecules such as salts will be quite easily removed with the ultrafiltrate. Furthermore, ultrafiltration alone does not increase renal excretion of sodium, and studies have shown a reduction in urinary sodium levels after ultrafiltration. Ultrafiltration reduces intravascular volume, which can stimulate the renin-angiotensin system. Renin-angiotensin results in retention of sodium and water and is counterproductive to the intention of ultrafiltration.

One author stressed the importance of a negative sodium balance in treatment of CHF (Haller 2000) While total body sodium is elevated in CHF, the neurohumeral axis responds to serum levels. Increasing serum levels will result in normalization of sodium excretion mechanisms, and, ultimately, urinary excretion of sodium. Others have actually given small boluses of hypertonic saline with diuretics and have found increased responsiveness to CHF treatment. (Forssell et al. 1980, Paterna et al. 2000). Yet another group has found that administration of an osmotic agent improved salt excretion. In a single case report of treatment of refractory CHF, urea was given. This resulted in increased salt excretion, increased diuresis, reduced body weight, and corrected sodium deficit (120 mmol/l to 136 mmol/l). (Cauchie et al. 1987) Thus osmotic gradients that favor mobilization of body sodium into the vascular space and thereby elevating serum sodium may be important for normalization of the neurohumeral axis.

Based on published results to date, it would appear that ultrafiltration must be used to treat CHF in combination with other means, typically drugs, to achieve the intended benefit. For instance, only those patients using ACE-inhibitors (which block the renin-angiotensin system) saw urinary excretion of sodium and continued reduction of body water. Guazzi et al. (1994) saw an increase in sodium urinary excretion after ultrafiltration, but one third of their patients had been on ACE-inhibitors, and all were on diuretics. Guazzi et al. concluded that ultrafiltration "may interrupt a positive feedback loop between salt and water retention and activation of the neurohumeral axis." Agostoni et al. (2000), noting weight loss four days after ultrafiltration (5.8 kg) was greater than the weight of fluid removed during ultrafiltration (3.9 kg), agree that restoring diuresis and response to diuretics is a key factor in treatment of CHF with ultrafiltration (most (22 of 28) of their patients were also on ACE-inhibitors). Even with pharmacological treatment, however, it appears that hyponatremia persists.

A company known as CHF Solutions is a leading advocate of the hemofiltration approach, and focuses on using hemofiltration to treat CHF fluid overload, removing 2 to 4 liters in a 4 to 8 hour period. Their system is very much like conventional hemofiltration used to treat renal failure (kidney dialysis therapy), though it is designed to avoid the use of anti-coagulants. The reusable equipment portion of the system costs about $10,000 per patient station and the disposables sell for $1,000 per patient. See, for example, published International Patent Applications Nos. WO 02/36068, WO 02/47609 and WO 02/053098, assigned to CHF Solutions, Inc., the disclosures of which are incorporated herein by reference. While the CHF Solutions technology may provide desirable attributes, it appears to be neither intended nor designed to address corresponding hyponatremia.

Finally, it can be seen that refractory CHF patients have the following features: 1) low serum sodium concentrations, 2) excess total body water, 3) excess total body sodium, 4) low blood pressure, and 5) non-responsive to medical treatment.

It would therefore be highly desirable to have a treatment regimen that could result in: 1) normalization of serum sodium concentrations to turn off signals to retain sodium, 2) increased urinary excretion of sodium after normalization of inappropriate neurohumeral signals to retain sodium, 3) a net loss of body water, primarily from the interstitial space, and 4) avoidance of excessive intravascular volume loss that can aggravate low blood pressure.

BRIEF DESCRIPTION OF THE DRAWING

In the Drawing:

FIG. 1 shows components of a system of the current invention, including a pressure monitor associated with a semipermeable membrane catheter, for use in treating compartment syndrome.

FIG. 2 shows a cross section taken along A—A of the catheter of FIG. 1.

FIG. 3 shows an enlarged detailed view of the distal end of the catheter of FIG. 1.

FIG. 4 shows a set of introducer components for use in the system of FIG. 1.

FIG. 5 shows components of an alternative preferred system of the invention adapted to provide a hydratable medium, for use in treating cerebral edema.

FIG. 6 shows a cross section taken along A—A of the catheter of FIG. 5.

FIG. 7 shows a cross section taken along B—B of the catheter of FIG. 5.

FIG. 28 is a table showing examples of suitable membranes.

FIG. 29 is a graph showing the relationship between sodium flux and final concentration.

FIG. 31 is a table showing varying combinations of processes.

SUMMARY OF THE INVENTION

Figure 8:
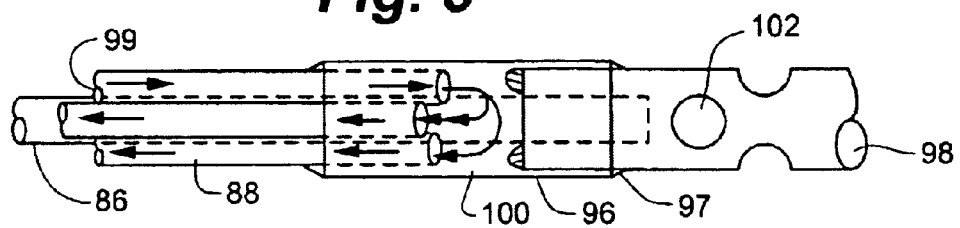
FIG. 8 shows an enlarged detailed view of the distal end of the catheter of FIG. 5.

A system of the present invention provides an integrated combination of features and functions for use in the therapy of tissue swelling, including edema, compartment syndrome and congestive heart failure. One preferred system comprises one or more recovery catheters comprising semipermeable membranes, in combination with recovery components for recovering bulk fluid or fluid components through the semipermeable membranes, and a hydratable medium, preferably in the form of a hydratable gas, adapted to be delivered to a lumen provided by the membranes under conditions suitable to remove water from the environment surrounding the membranes. In yet another preferred system, the semipermeable membrane and hydratable gas are used in an extracorporeal fashion, e.g., with the gas provided either within or surrounding hollow fibers, in order to withdraw water vapor from fluid (e.g., blood, ultrafiltrate, etc.) that is contacted with the opposite fiber surface.

The membranes can be positioned in any suitable position with respect to a tissue exhibiting swelling, including directly within the tissue itself, within a remote tissue (e.g., circulating blood) having an indirect physiologic effect on the tissue exhibiting swelling, or externally to the body itself, as in the form of a remote (e.g., extracorporeal) unit functionally connected to the body, as by a fluid (e.g., hemofiltration) flow circuit, and in turn to the swollen tissue site. Optionally, the system also includes one or more introducing components, as described further herein.

In a particularly preferred embodiment, where the catheters are positioned directly or indirectly within a tissue site exhibiting swelling the system comprises:

a) one or more recovery catheters comprising semipermeable membranes, each of such semipermeable membranes being preferably in the form of a hollow fiber, b) recovery components for recovering bulk fluid or fluid components (e.g., water) through the semipermeable membranes and from the tissue site, in order to achieve a therapeutic result, preferably in the form of a reduction in swelling, and either c) a hydratable medium, e.g., filtered or dehydrated gas, adapted to be delivered to the tissue site and within the semipermeable membrane(s) under conditions suitable to remove water from the tissue site in the form of hydrated medium, or d) one or more components of a monitoring system associated in an integral fashion with the recovery catheter(s).

In a particularly preferred embodiment, the system provides one or more introducing components adapted to position the recovery catheter(s) within a tissue site, and preferably directly within a site exhibiting swelling. In a further preferred embodiment, the system includes the hydratable medium of feature (c) above, and even more preferably it includes both features (c) and (d) in combination.

Various embodiments of this invention, and particularly those that employ the hydratable medium described herein, permit one to perform "water removal therapy" (or for short, "WRT") in order to remove substantially only water from biological fluids. By removing only water, all other biologic agents, including essentially all solutes and formed blood elements (such as cells) are increased in concentration in the remaining bodily fluid(s). WRT can be applied to several clinical conditions in which there is an actual excess of water, and therefore used therapeutically, or a potential accumulation of water (as in compartment syndrome), and therefore used in a prophylactic fashion. Water removal of this type cannot typically be accomplished by any other clinical method.

In a particularly preferred embodiment, the present invention therefore includes a functional, and ideally physical, combination of ultrafiltration and water removal, and more preferably where both are performed using semipermeable hollow fibers positioned within corresponding extracorporeal circuits. Both UF and WRT can be performed in any suitable manner, e.g., in series or parallel, and with one or both being performed in an extracorporeal circuit, as compared to intravascular manner.

In yet another embodiment, an intravascular access catheter is composed of hollow fiber membranes. Thus, ultrafiltration occurs within the blood vessels. Ultrafiltrate is removed and passed through an extracorporeal WRT cartridge. The embodiment provides the advantages of reduced viscosity of the fluid entering the WRT cartridge, and no intravascular loss of formed blood elements (essentially no blood priming volume). Concentrated plasma ultrafiltrate can be returned to the intravascular space. See, for example, International Journal of Artificial Organs, Volume 22, number 5, 1999, pp 342–346, Extracorporeal therapies: C. Ronco.

In other preferred embodiments, blood is removed from the vessels and passed through one or more extracorporeal cartridges containing semipermeable membranes (typically in the form of hollow fibers). Extracorporeal circuits of a type used for hemofiltration in the course of congestive heart failure can be adapted and used in a system of the present invention. Applicant has found that extracorporeal WRT allows the use of a large cartridge, that can accommodate correspondingly higher rates of water removal if indicated. A system of this invention can also be adapted, for instance, for arteriovenous and/or venovenous use.

Some or all components of a system of this invention can be adapted for intravascular use as well. Intravascular WRT is possible, for instance, at low water removal rates, while intravascular UF, follow serially by extracorporeal WRT, offers several advantages.

As described herein, WRT can be used in combination with one or more other treatment processes as well, including ultrafiltration, hemodialysis and reinfusion, in order to achieve desired results.

WRT followed by ultrafiltration or hemodialysis, for instance, can allow greater separation of toxic agents. Hemodialysis can be of a form commonly used for chronic renal failure in which blood flows through a hollow fiber while another liquid (dialysate) flows outside the hollow fiber. Exchange occurs between blood and dialysate by diffusion from high concentrations to low concentrations. Agents that are to be removed from the blood are absent in the dialysate; likewise agents to be delivered to the blood have high concentrations in the dialysate. Clearance of some agents may be enhanced by first concentrating the solution using WRT and then performing dialysis, particularly since a greater mass transfer can be achieved with concentrated rather than dilute elements. Since WRT will tend to concentrate all elements in the remaining fluid, it will allow greater removal of those elements with subsequent treatment. Clinical examples of this application include the removal of toxins, poisons, endotoxins, or other noxious agents.

In a further preferred embodiment, a system of this invention that includes the hydratable medium of feature (c), is used in cooperation and combination with an intravascular or extracorporeal hemofiltration process and system. The resulting combination can provide an optimal combination of the both tissue water removal, by vaporization, as well as ultrafiltration of bulk fluid, including fluid components below a desired size and/or molecular weight cutoff. This combination of both ultrafiltration (of water and small solutes) and vaporization (of substantially water only) can be performed either sequentially and/or simultaneously, and on either the same or different aliquots of bodily fluid, with either or both processes being performed either in situ within the body or in an extracorporeal fashion.

When WRT is used in combination with ultrafiltration, a desired and controllable combination of water and mass removal can be achieved. Specific combinations of water and mass cannot be accomplished by any other conventional methods without extensive plasma water turnover. WRT can be applied to congestive heart failure, acute and chronic renal failure, hyponatremia, water excess syndromes (including Syndrome of Inappropriate Antidiurectic Hormone "SIADH" and water intoxication), and other systemic conditions. By specific placement of access catheters, WRT can also be applied to organ-specific conditions of edema such as Acute Respiratory Distress Syndrome or Acute Renal Failure by placement of vascular access catheters in the vena cava or aorta, respectively. In turn, WRT can result in increased serum sodium levels while removing total body water while maintaining low plasma turnover. WRT in combination with ultrafiltration can produce removal of body water and direct removal of sodium while increasing serum sodium concentrations to normal levels. WRT results in retention of desired (and optionally all) solutes in the blood. Thus, not only is there a slight increase in colloid osmotic pressure (as seen in ultrafiltration) but also a slight increase in crystalloid osmotic pressure. The result is more even refilling of the intravascular volume, with a net therapeutic effect.

Removing fluids from the intravascular space causes excess interstitial fluid to flow into the vascular space, in a process referred to as "interstitial refilling". If the rate of fluid removal from the body or blood exceeds interstitial refilling rates, intravascular blood volume will fall, and patients will experience hypotension. In turn, agents that are found primarily in the blood vessels (albumin, protein, and hemoglobin) will increase in concentration. If vascular refilling from the interstitial space equals the rate of water removal, however, the concentration of intravascular agents will not change. Thus, large agents that are not found in the interstitial space and that are not removed by treatment can be used to monitor fluid status. Since neither WRT or UF are typically designed to remove these large agents, both will result in increased concentration of hemoglobin if fluid removal rates are excessive.

As compared to UF, only WRT is designed to remove substantially only water, though both WRT and UF cause interstitial refilling. Because salts are not removed from the vascular space, but are brought into the vascular space from the interstitial space, WRT will result in an increase in salt concentration even at low levels of treatment. UF will bring salt into the vascular space with refilling, but there remove salt at the same concentration level in the blood.

Using a combination of UF and WRT, therefore, both mobilization of interstitial fluid and salt, and elimination of salt will occur. During treatment, serum sodium can be monitored. Treatment will be stopped when sodium levels normalize, and thus potassium and magnesium levels will also be normalized. Improved sodium levels in the blood stream will signal natural mechanisms to increase sodium excretion via the renin-angiotensin systems. Thus, normalization of the neurohumeral axis may be the primary benefit of ultrafiltration, and increased serum levels of sodium as provided by WRT may be more effective in accomplishing that goal.

DETAILED DESCRIPTION

The present invention further provides a method of preparing such a system by the fabrication and/or combination and functional assembly of its various components, and a method of using such a system to achieve a therapeutic result, as well as various components and subcombinations thereof, several of which are considered to be novel in their own right. The system and method can be used to directly or indirectly treat a tissue site exhibiting swelling.

When used to directly treat a site of swelling, for instance, the semipermeable membrane(s) will typically be positioned within a region that itself exhibits swelling. When used to indirectly treat a site of tissue swelling, the semipermeable membrane(s) can instead (or in addition) be positioned and used in a site remote from (including externally to), but physiologically associated with, the swollen tissue. For instance, the system can be used to dehydrate tissue fluids, such as blood (e.g., intravascularly) or CSF (e.g., intraventricularly), that are physiologically associated with swollen tissue, leading to dehydration of those tissues as well, and ultimately, to a reduction in swelling. The system can be used for the removal of excess fluid in a variety of situations, including pulmonary edema, congestive heart failure, acute renal failure, ischemic heart disease, as well as in cerebral edema and compartment syndrome.

A recovery catheter of this invention comprises at least one, and preferably a plurality, of semipermeable membranes. As used herein, the term "semipermeable membrane" will generally refer to a membrane forming some or all of the wall of a microcatheter (e.g., "hollow fiber"), preferably with a substantially open lumen having at least one open end accessible to liquid or fluid flow within the lumen. The membrane portion itself is adapted to permit the passage of bulk tissue fluid or fluid components (e.g., water), while substantially precluding the passage of cells or nonfluid tissue. Such passage can be accomplished using any suitable means, e.g., through pores provided by the membrane itself, as well as by the preparation of membranes having suitable chemico-physical properties (e.g., hydrophilicity or hydrophobicity) to effectively control passage of fluid and its components in a predictable and desired fashion.

The introducing components, in turn, can include any introducing component, or set of components, that is suitable and adapted to position the recovery catheter(s) within a tissue site, and preferably within a site that itself exhibits swelling. Such components can be provided, for instance, in the form of a totally or partially circumferential covering (e.g., stationary or removable delivery sheath), and/or by the inclusion of one or more components (e.g., stylets) positioned internally, adjacent to, and/or along the length of the semipermeable membrane(s) and designed to impart sufficient properties (e.g., stiffness, lubricity) to the overall catheter assembly or portions thereof.

Finally, a system of the current invention includes recovery components for moving and/or recovering bulk fluid or fluid components (e.g., water) through the semipermeable membranes and/or from the tissue site, in order to achieve a therapeutic result at a site of tissue swelling. The movement of fluid or fluid components can be considered to occur in up to at least three modes, including 1) the movement of interstitial fluid within the tissue itself (e.g., by convective flow of interstitial fluid toward a semipermeable membrane positioned therein), 2) the movement of fluid from the tissue and through a semipermeable membrane(s) positioned therein, e.g., by diffusion or convection through the membrane wall and into its lumen), and 3) the movement of fluid from or within the semipermeable catheter(s) (e.g., to a remote site, typically outside the body).

A recovery component of this invention can be provided in any suitable form or combination of forms, including by the use of hydrostatic pressure, diffusion, and combinations thereof, and can be designed to affect any or all of these modes of fluid transport. Hydrostatic pressure, for instance, can be provided as either negative hydrostatic pressure (vacuum or suction) and/or in the form of positive hydrostatic pressure. Diffusion, in turn, can be accomplished using the physical-chemical forces that result from the proximity of two different media, or forces that occur within a suitable membrane positioned at a liquid/gas interface. Such forces result, for instance, in the diffusion of water through the membrane and into the gas, on the basis of either vapor pressure of the liquid itself and/or of liquid components, e.g., volatile compounds such as ketones, as in diabetic coma, or ammonia (including in its various forms, including ammonium hydroxide), as in the course of liver failure.

Hydratable Medium

The system further includes components for providing a hydratable medium or a physiological monitor, or preferably, both. In one preferred embodiment, a system of this invention permits fluid to be effectively withdrawn from the tissue site by the delivery of a medium adapted to be hydrated by, and upon contact with, moisture within the tissue site. In turn, the removal of moisture from the tissue site, upon the removal of hydrated medium, preferably achieves, or contributes to, a therapeutic effect brought about by a reduction in swelling. The word "hydratable", as used in connection with an embodiment of this invention, will refer to a medium capable of being converted from a state of lower moisture content (e.g., lower relative humidity for a gas) to a level of detectably greater moisture content ("hydrated"), by the accumulation of water (e.g., in the form of vapor or liquid) from within the tissue.

The present invention provides a method and system for the delivery of a medium to a tissue site, under conditions suitable to permit the medium to be hydrated by moisture, e.g., within the tissue site, in order to achieve a therapeutic effect upon the withdrawal of hydrated medium from the site. In a particularly preferred embodiment, the medium comprises a gas that can be delivered in a relatively less hydrated (e.g., desiccated or tending toward desiccated) form, and recovered in a more hydrated (e.g. saturated or tending toward saturated) form.

In both such embodiments, the medium is preferably delivered within one or more semipermeable interface materials, preferably in the form of membranes or catheters (e.g., hollow capillary fibers), each having a lumen formed, in whole or in part, by wall portions adapted to permit the accumulation of moisture (and optionally, small solutes), between the tissue and the lumen, while substantially preventing the unrestricted flow of bulk fluids therebetween. One or more catheters are used to form an insertable catheter assembly that can include associated protective and/or placement catheter portions, and conduits providing lumen for the delivery and/or recovery of hydratable gas, as well as negative pressure. In another embodiment, a plurality of hollow fibers can be used to prepare a cartridge for extracorporeal use, in which case the tissue (blood) is contacted with the fibers outside the body, to be treated there and subsequently returned to the body.

The system of this invention, and corresponding catheter assemblies, can be designed to permit the hydration of the medium (as by vaporization of the water component of blood) to occur either as the dehydrated medium is traveling toward and/or away from the distal catheter tip, and to a distal air plenum. In each case, typically a single impermeable lumen will serve to transfer the gas in the opposite direction, e.g., to return hydrated gas from the plenum or deliver dehydrated gas to the plenum, respectively.

The catheter(s) can be provided in any suitable form and configuration, e.g., as one or more closed and/or open ended individual fibers, as a plurality of closed and/or open ended parallel fibers, and/or as circuitous loops of fibers. In such configurations, the lumen of each catheter will typically include an entry orifice for the delivery of hydratable gas and a recovery orifice for the recovery of hydrated medium from the lumen.

The fibers can be delivered to the tissue site using any suitable introducing components, e.g., they can be positioned within a surrounding placement catheter (e.g., conventional ventricular catheter or customized introducer) that can itself be removed or permitted to remain in place in the course of using the delivery/recovery catheter. Optionally, or in addition, the delivery/recovery catheters can be accompanied by one or more delivery guidewires, stylets, or trocars, and combinations thereof, e.g., adapted to position the semipermeable membrane(s) within the tissue site.

An apparatus and system of this embodiment finds particular use in the treatment of cerebral edema. While not intending to be bound by theory, it appears that an increase in brain tissue water content occurs after brain injury. Osmotic pressure exerted by intracellular osmolarity, estimated to range between 317 and 587 mm Hg in ischemic tissues (Kobari et al., 1985), creates a gradient for the movement of fluid into cells after ischemic injury, leaving large, osmotically active behind in the extracellular spaces (Odland, Sutton, 1999). Such osmotic fluid shifts after ischemic or traumatic injuries may underlie the frequent failure of contemporary therapy to attenuate cerebral edema.

Clearance of edema fluid from tissue to CSF is considered to be a primary mechanism for the resolution of vasogenic brain edema. Hydrostatic pressure gradients are important for fluid movement in the extracellular space, though these hydrostatic pressure gradients become less effective if there is cellular swelling. To date, very few authors have suggested that the manipulation of CSF osmolarity can influence cerebral edema formation after brain injury. See, e.g., Onal et al. 1997, in which the administration of a bolus infusion of albumin into the cerebral ventricles resulted in a significant reduction of tissue water content at 6 hours post injury. Although the effect was transient, and could not be repeated at 24 hours post injury, these results nevertheless support Applicant's suggestion that increasing the osmolarity of CSF after brain injury, by even a small amount, can increase movement of water into the CSF and thus reduce edema.

In one preferred embodiment, therefore, the system of the present invention can be used to counteract the gradient that is thought to result from water movement into tissue, and following injury. Water can be directly and effectively removed from within the cerebral ventricles, and indirectly from the tissue, to decrease tissue edema. With the removal of water from the ventricles, by vaporization into a hydratable gas, fluid can be pulled from the edematous brain tissue.

If water vaporization rates do not exceed tissue edema reduction rates, the osmolarity and colloid osmotic pressure of the CSF will remain constant. With such a method, both crystalloid and colloid osmotic pressure can increase, in a manner sufficient to maximize the relative effects of both types of pressure in the reduction of edema.

The system of the present invention also preferably provides a hydratable medium, suitable for use in removing water or volatile compounds (e.g., ketones or ammonia in its various forms) from the lumen of hollow fibers. Any medium that passes through the lumen of the hollow fibers can sweep the vapor clear. The rate of flow of the transport media can affect removal, as can water capacity of the media. Gaseous media have much greater flow rates for similar pressure gradients, and are typically more preferred for many embodiments of the present system.

Several gases can be used to sweep away vapors from within the lumen of hollow fibers of the present invention. The selection of a suitable gas can include consideration of both the effect of the gas on the tissues, and the physical properties of the gas itself. With respect to tissue effect, a suitable gas for use in this invention preferably has no deleterious effect on tissue, under the conditions of use. Rather, the gas is either inert with respect to tissue, or can have a favorable effect, such as the effect of oxygen in improving oxygenation of the tissues. Carbon dioxide is typically less preferred, particularly under conditions where it might increase acidosis, but it may also have some vasodilatory effects that may be beneficial.

A gas suitable for use in the system of this invention preferably also provides an optimal combination of physical properties, including chemical inertness and stability, water content, and the ability to be provided in sterilized form. Air is readily available, and can be dehydrated and filtered for sterility. Nitrogen is inert, commonly available, and as a compressed gas would be of low humidity. Helium is an inert gas with very low density, and thus low resistance to flow. High flow rates can be achieved while maintaining low Reynolds numbers. Those skilled in the art will also appreciate the manner in which temperature will affect the humidity of all gases, and a resistor to drop pressure may also be used in order to reduce gas humidity.

In addition to water, other volatile compounds may be removed from, or delivered to the tissue, in order to achieve a therapeutic effect using a system of this invention. Examples include removal of ketones in diabetic coma, removal of ammonia in hepatic coma and liver failure, and removal of urea in renal failure. Similarly, mixtures of hydratable gases can be used in order to effectively deliver beneficial agents, such as nitric oxide or oxygen, to the tissue site.

In a further preferred embodiment, the system of this invention, including a hydratable medium, is used in an extracorporeal process and system to remove substantially only water. WRT can be combined with hemofiltration, for instance, in order to provide an optimal combination of bulk fluid recovery, as provided by hemofiltration, with the vaporization and removal of water by WRT, to the controlled exclusion of electrolytes and larger constituents. This combination of both ultrafiltration and vaporization can be performed either sequentially and/or simultaneously, and on either the same or different aliquots of bodily fluid. In such an embodiment, the present system and method can be used to perform treatment in a manner that removes only water, or in a manner that removes both water soluble components, in a controllable manner and to the extent desired to achieve a therapeutic effect.

In one such embodiment, the method can be used to remove water by circulating dry air through hollow membrane fibers that vaporizes water in the blood. The water vapor is then swept out of the membrane fiber with the constant flow of dry air. The benefit of there being substantially no salt removal will be particularly beneficial to those CHF patients having low salt concentrations in their blood. About one third of hospitalized patients have sodium levels below normal, and low sodium levels are a risk factor for death due to CHF. Other cation concentrations are frequently low in CHF patients as well, particularly potassium and magnesium, and retention of these cations will be similarly improved.

Increasing ions in the blood will tend to increase crystalloid osmotic pressure, which in turn will have the effect of increasing the rate of vascular refilling. Although ion concentration is increased in the blood, bulk flow of interstitial fluid into the capillaries will prevent diffusion of ions into the interstitial space. WRT can also be accomplished with a microcatheter placed directly into the vascular space. Alternatively, an ultrafiltration catheter can be used to remove plasma directly from the vascular space, with WRT being performed on the ultrafiltrate and/or on separate aliquots of whole blood.

By contrast to conventional hemofiltration, which typically does not improve low salt concentrations, a system of the present invention will remove body fluid while retaining salt in the vascular system. Increased urine output will occur by 1) increased responsiveness to loop diuretics (which require sodium), 2) correction of inappropriate signals to retain water and salt, and 3) increased blood pressure.

In one preferred embodiment, therefore, the present invention provides a functional combination of water recovery therapy, ultrafiltration and optionally, reinfusion. These processes can be performed simultaneously (e.g., in parallel) and/or in any suitable order (e.g., in series), and on either the same or different tissue samples or sites. WRT and diffusional hemodialysis, ultrafiltration, and reinfusion (replacement fluids) can be used in varying combinations in order to provide increased exchange by the creation of concentration gradients. See, for instance, Table II showing various advantages associated with varying combinations of these processes, including varying combinations and/or sequences, of WRT with other processes, as well as various embodiments of WRT per se. These options include, for instance, those in which a hydratable medium is delivered within the intraluminal space, as compared to extraluminal space, of a collection of hollow fibers within a cartridge. In the first column of Table II, the particular processes are identified, generally in the order in which they will be applied to blood or other bodily tissue. The following two columns describe the relative positions of blood, desiccated gas, ultrafiltrate, etc. with respect to the fibers within corresponding cartridges, and the final column provides related comments, including potential advantages, associated with each.

Extracorporeal circulation can be used to reduce generalized body fluid overload, and also can target specific organs, depending on placement of the withdrawal and infusion catheters. For example, catheters placed in the vena cava will have more specific effect on pulmonary edema and myocardial edema. Catheters placed in the aorta proximal to the renal artery distribution will have a specific affect on renal edema.

Several features of WRT make it amenable for outpatient, or even home use. Arteriovenous hemodialysis relies on the pressure differential between arterial and venous blood to drive blood through the cartridge. The same method can be used with WRT. Given wide spacing of hollow fibers, low pressure airflow can remove water at sufficient rates to allow daily or weekly preventive treatment. The low flow of this system may require an internal heater to maintain blood at normal temperatures. WRT of ultrafiltrate can be appropriate for this application, particularly to reduce viscosity, and possible sludging.

Venovenous treatment can be performed with pumping action of vaporization itself. Normally, venovenous ultrafiltration requires the use of a mechanical pump to move blood out of the vein, through the cartridge, and back to the vein. Vaporization itself can provide pumping action by using a proximal switch valve and distal check valve. During vaporization with the proximal valve closed and subsequent loss of water volume within the hollow fibers, hydrostatic pressure will fall inside the hollow fibers. Periodic opening of the proximal switch will refill the cartridge. Emptying the cartridge and return of blood to the vein is accomplished by gravitational flow and reduced venous pressure. Thermal effects will also contribute to blood flow within the system. Cooling of blood occurs with WRT. Thus, the effluent will be cooler and more dense than afferent blood. The cool blood will be sink at a higher rate. Compliance of the hollow fibers will avert the need for venting. Because blood flow through the cartridge will be at low flow rates, an internal heater or other suitable means can be used to maintain blood temperature and therefore water vapor pressure.

Transdermal WRT is an option as well. WRT can be performed without the need for intravascular access, although typically at lower rates. Methods to increase skin conductivity could allow transdermal treatment. Transmucosal water loss is also possible. Subdermal interstitial fluid can be accessed by micropuncture and other suitable means.

Various aspects concerning WRT can be assessed using the following mass transfer formula. This formula has particular applicability to the preferred embodiment in which blood or other fluid is passed through the lumen of one or more hollow fibers, and hydratable medium (e.g., desiccated gas) is passed in the extraluminal space surrounding such fibers.

Various aspects concerning WRT can be assessed using the following mass transfer formula. This formula has particular applicability to the preferred embodiment in which blood or other fluid is passed through the lumen of one or more hollow fibers, and hydratable medium (e.g., desiccated gas) is passed in the extraluminal space surrounding such fibers.

$$\text{Water removal rate/fiber=flow (concentration out}-\text{concentration in)}$$

More particularly, the following formula for water mass transfer in pertains to gas flow within the hollow fibers:

$$\text{Water removed per fiber}=Q((1-e^{-2kl/rv}*Cw_{saturated})-Cw_{intake})$$

where Q is the rate of airflow through the fiber (in $m^3$/sec), $Cw_{saturated}$ is the equilibrium vapor concentration (in mmoles water/$m^3$) based on water vapor pressure of tissue at 37 degrees C., $Cw_{intake}$ is the concentration of water vapor (in mmoles water/$m^3$) in air entering the system, l is the length of the hollow fiber (in meters), r is radius (in meters), and v is the flow velocity (in m/sec), and k is the mass transfer coefficient determined for the particular fibers and conditions of use.

A corresponding formula can be used in the alternate embodiment, in which desiccated gas will flow outside the hollow fibers, with blood or other liquid flowing within.

$$\text{Water removed per fiber}=Q((1-e^{-2klr/(r2-r2)v}*Cw_{saturated})\text{-}Cw_{intake}))$$

Water removal with blood or ultrafiltrate in the hollow fiber and gas outside the hollow fiber can be modeled as above. The surface area and mass transfer coefficient are unchanged. The variable to consider is cross-sectional area outside the fiber available for airflow. In this model of coaxial cylinders, increasing the cross sectional area reduces velocity, so there is no change in water removal for a given airflow. Increased cross-sectional area will reduce resistance to flow, so airflow will improve with larger spaces between the fibers.

Based on this formula, it can be seen that increasing airflow can often be the simplest and most efficient means of increasing water removal. Even though the air coming out of the system will be less than completely saturated, that inefficiency can be more than compensated by the increased volume of gas recovered.

Given this formula, it can be seen that a number of variables can be considered and adjusted as necessary, in order to achieve water removal at any desired rate and and/or total amount. For instance, in order to achieve water removal at a rate within the currently preferred range of about 100 ml/hr to about 500 ml/hr, and employing a corresponding number of fibers.

For instance, given this rate of water removal, Q can be provided in the range of from about $10^{-8}$ to about $10^{-5}$ and more preferably from about $10^{-7}$ to about $10^{-6}$. $Cw_{saturated}$ is between about 0.1 to about 50 mmoles water/m3, and more preferably between about 5 to about 20 based on water vapor pressure of tissue at 37 degrees C.

$Cw_{intake}$, though expressed in mmoles water/$m^3$, can be determined from corresponding dewpoint values (where dewpoint is the temperature at which air must be cooled for condensation to occur). With increasing amounts of water in the air, it can require only a slight reduction in temperature to cause condensation. If the air is fairly dry, it requires colder temperatures to produce condensation. Dewpoint, in turn, can be converted to g/$m^3$ or mmoles/$m^3$. The experimental results below show that even relatively moist gas can be used effectively, so long as its velocity is sufficiently high. Hence where the hydratable medium is air or similar gas, its dewpoint is preferably less than about 10, and more preferably less than about 1.

| | Dewpoint, ° C. | g/$m^3$ | mmoles/$m^3$ |
|---|---|---|---|
| Very dry air (desiccated) | −73 | 0.003 | 0.17 |
| Relatively dry air | 0.39 | 5 | 278 |
| 50% relative humidity at room temperature | 11.3 | 10.2 | 567 |

The length (l) of the fibers can be on the order of about 1 cm to about 100 cm and preferably is between about 5 cm and about 20 cm. The radius (r) is typically derived using fibers having an inner diameter (ID) of between about 50 microns to 5000 microns, and more preferably about 100 microns to about 1000 microns, The flow velocity v of gas within the fibers can be between about 1 l/min to about 100 l/min, and preferably between about 2 l/min and about 25 l/min, all per 1000 $cm^2$ of fiber surface area, and k can be on the order of about 0.1 to about 50, and more preferably is between about 2 and about 20. Given a particular water removal rate, per fiber, the total water removal then becomes largely a function of the number of fibers employed. An extracorporeal cartridge for use in the present invention will typically include between about 1 and about 10,000 such fibers more preferably between about 1,000 and about 5,000 fibers.

Suitable monitors include, but are not limited to, those adapted to qualitatively and/or quantitatively assess various parameters, preferably in a substantially "real time" fashion during and in the course of using a system of this invention. Such parameters can include physiologic parameters associated with the tissue itself, as well as performance parameters associated with the function of the system or its components. Examples of suitable physiologic parameters include, but are not limited to, tissue pressure (total and partial pressures), blood flow, hydration (water content), temperature, pH, sodium, and biochemical parameters (e.g., myoglobin levels).

Such parameters can be determined using any suitable means, for instance, pressure can be determined using conventional fluid column techniques (e.g., diaphragm or manometer), or fiberoptic techniques, while fluid (including blood) flow can be determined using near IR spectroscopy and laser Doppler techniques, and tissue hydration can be determined by a variety of means, including the placement of a suitable probe or electrode to determine electrical impedance.

In a particularly preferred embodiment, the monitoring components are "associated" with the system of this invention, in the sense that one or more portions of the monitoring components are physically and/or functionally integrated with the placement and/or operation of the semipermeable membrane component. As shown in the preferred embodiments of FIGS. 1–4, for instance, the overall catheter assembly is configured to provide a fluid column component for the determination of tissue pressure. Typically, the associated components of such monitoring components will in turn be used with other, conventional, components, such as conduits, connectors and monitors. For example, the Figures depict the manner in which components of a conventional pressure monitoring system (available from Stryker) can be readily adapted for use with a system of this invention.

When used for the treatment of cerebral edema, a system of the present invention can include monitoring components for a variety of parameters. In a preferred embodiment, the parameter is that of intracranial pressure or ICP. In adults, the average ICP ranges from 0–10 mm Hg. 20 mm Hg is considered to be the maximal upper limit of tolerable ICP and pressures exceeding 40 mm Hg are considered extremely elevated. The type of monitor used is dependent on a number of clinical factors, not the least of which is the neurologic disease causing the pressure increase.

Suitable materials for use as semipermeable membranes of the present invention provide an optimal combination of such properties as mass transfer properties, biocompatibility, surface-to-volume ratio, processability, hydrophobicity and hydrophilicity, strength, transport rate, and porosity. Examples of suitable hollow fibers are described, for instance, I. Cabasso, "Hollow-Fiber Membranes", pp 598–599 in *Kirk Othmer Concise Encyclopedia of Chemical Technology*. In a preferred embodiment, such membranes are provided in the form of "hollow fibers" or "microcatheters", having walls (or portions thereof) formed of such membrane material. In alternative embodiments, the membranes can be provided in any suitable form or configuration, e.g., in the form of pleated or corrugated membrane sheets, and the like, preferably positioned within and/or by a recovery catheter. In situations where the semipermeable membrane(s) are provided in other than circumferential (e.g., fiber) form, the hydratable medium can be delivered to a major surface of the membrane, opposite the surface in contact with, or accessible by, the tissue fluid itself.

The dimensions of a hollow fiber will depend largely on the intended use of the apparatus. In a number of preferred embodiments, a hollow fiber will be provided in the form of a capillary having an outer diameter of between about 0.1 mm and about 10 mm, preferably between about 0.2 mm and about 3 mm, and more preferably between about 0.3 mm and about 1 mm. Such capillary fibers preferably also provide a substantially open lumen, defined by an inner fiber diameter that is typically on the order of 50% or more, and preferably 70% or more the corresponding outer diameter.

Such membranes preferably also provide permeability cutoffs suitable for use in the intended application. The permeability of hollow fiber membranes for use as microdialysis fibers is generally phrased in terms of kiloDaltons (and can range between about 10 kD to about 1000 kd). By comparison, the permeability of fibers used for ultrafiltration is typically considerably greater, and hence phrased in terms of microns, with typical ranges from about 0.1 micron (corresponding roughly to the 1000 kD cutoff at the higher range above) to about 1 micron. Fibers suitable for use in the system of the present invention, therefore, typically provide permeability in the range of from about 1 kD to about 200 microns, preferably from about 10 kD to about 10 microns, and more preferably between about 50 kD and about one micron.

Permeability can be determined using suitable techniques, such as conventional wet sieving techniques. See, for instance, Spectrum Laboratories, Inc. product information which describes the manner in which both the membrane molecular weight cut-off (MWCO) and pore size are related and can be determined.

Hollow fiber performance can be characterized by the molecular weight at which 90% of the solute will be retained (prevented from permeating) by the membrane. This value is called the Molecular Weight Cut-Off (MWCO), which in turn is described as the molecular weight of the largest globular protein that can pass through the pores of the membrane. In general, proteins that weigh more than the MWCO will be retained by the membrane. In addition to the molecular weight, the permeability of a particular solute is dependent on the shape of the molecule, its degree of hydration, and its charge. Each of these may be influenced by the nature of the solvent, its pH, and its ionic strength.

The MWCO is controlled, in turn, by the size of the pores in the membrane. Separation efficiency is influenced by the pore size distribution and the presence of a substantial number of pores much larger than the average will allow leakage of high molecular weight solutes. Thus, a narrow pore size distribution is highly desirable.

The cross-sectional structure of such membranes is either symmetric or asymmetric depending on the type and use. Symmetric membranes, such as dialysis tubing, have pores of the same diameter throughout their thickness while asymmetric membranes, such as unsupported flat sheets, have smaller pores that control the MWCO in a very thin layer or skin at one surface and larger pores in the remainder. The pore size distribution is equally important in the two types.

Sample flow perpendicular to the membranes, renders the membrane susceptible to blockage. The phenomenon can be reduced by sample mixing during filtration. Mixing can be achieved by either stirring or by passing the sample parallel to the membrane.

Semipermeable hollow fibers suitable for use in the system of the present invention can be prepared using conventional methods, and are available commercially. Hollow fibers are typically provided in the form of minute tubules, the entire walls of which are constructed of a semipermeable material. The material, in turn, will typically determine what can or cannot pass through the wall of the tubules. The selection of hollow fiber material is based primarily on the size of molecules to be removed or retained, as well as other physical properties. By comparison, reverse osmosis (RO) membranes have even smaller pores than either microdialysis or ultrafiltration. Reverse osmosis is typically performed with excessive pressures, and is therefore not widely used for clinical treatment. RO membranes are used for removing salt from water, and purifying water. The pores are small enough that only water can pass through (a hydrated water molecule being approximately 0.04 microns diameter). With the small pore size, water flux through the membrane is also limited. For purposes of the present invention, RO membranes are generally less preferred, however, if only in view of their limited availability and high hydrostatic pressure requirements.

Water vapor and other gases will pass through very thin silicone or other materials. These membranes have no open pores, yet allows water vapor to pass through the very thin, permeable membranes. The rate of water removal is reduced, but the possible advantage is that no bulk flow can occur, even after a period of wetting or exposure to transmembrane hydrostatic pressures. Yet other membranes used for water vapor removal do have pores, but the pores do not allow liquid water to pass. Pores in hydrophobic materials do not wet, for instance, but instead allow vaporization at the liquid water-vapor interface within the pores.

Such hydrophobic materials can be provided, for instance, in the form of microporous hydrophobic membranes (MHMs), of the type described in Goldberg et al., "Design Solutions Using Microporous Hydrophobic Membranes", Medical Devices and Biomaterials Magazine 1997 (http://devicelink.com/mpb/archive/97/03/002.html). Numerous polymers can be employed to form MHMs. Today, the predominant polymers used are PTFE (polytetrafluoroethylene), polypropylene, PVDF (polyvinylidene difluoride), and acrylic copolymers. All of these polymers can be treated in order to obtain specific surface characteristics that can be both hydrophobic and oleophobic (repelling liquids with low surface tensions).

The Goldberg et al. article describes the manner in which MHMs block liquids, while allowing air or gases to flow through the membrane. The low surface tensions of MHMs cause them to repel fluids from the surface, leaving the pores of the membrane filled with air. The porosity of the membrane allows air to flow freely through the material. Because of their diverse surface tensions and microstructures, membranes made from various polymers have significantly different properties, including chemical inertness, water-entry pressures, airflows, and surface release characteristics. The hydrophobic nature of an MHM prevents fluid from passing while allowing air to flow freely across the membrane, facilitating accurate pressure measurements.

Those skilled in the appropriate art will understand the manner in which the choice of a particular MHM will depend on a number of design considerations, and will include such considerations as fluid containment, fluid surface tension and fluid pressure. Other considerations, of particular relevance to the present invention, will include airflow rates, surface area, temperature, sterilization method (e.g., MHMs can be sterilized by autoclaving, ethylene oxide, or gamma irradiation), life expectancy, biocompatibility and chemical compatibility, as well as membrane quality and consistency.

There are many parameters used to characterize the functional attributes of specific MHMs. Listed below are some of the key terms and their definitions: Water-Entry Pressure (WEP). Also known as water breakthrough, WEP is the pressure required to force water through a hydrophobic structure. This property is typically expressed in pounds or bars per square inch. Gurley Value. This variable provides a reliable measure of the airflow through an MHM. Usually expressed in seconds, the Gurley value will describe the length of time a specific volume of air under a specific pressure takes to pass through a specific area of an MHM. Bubble Point. Used to characterize the MHM's reference pore size, the bubble point is the lowest pressure that is required to displace a low-surface-tension fluid from the pore structure of an MHM, and is typically expressed in pounds or bars per square inch.

MHMs can be sealed to plastic devices using several different methods. Depending on the device material and the polymer makeup of the MHM, alternatives can include ultrasonic welding, radio-frequency (RF) sealing, heat sealing, insert molding, or adhesive bonding.

Ion-exchange polymers are another class of useful membrane materials that are typically used in electrodialysis. They have cation and anion groups within the matrix that can assist in water vaporization and removal processes. These materials are described in "Electrodialysis", T. A. Davis and D. A. Glassner, Handbook of Downstream Processes, Blackie Academic & Professional, London, Elliot Goldberg editor, pages 140 to 166.

In a preferred embodiment, the system of the present invention accomplishes the removal of water, by tissue ultrafiltration, as a therapeutic treatment. Removal of substantially only water can be accomplished by use of RO membranes or water vaporization. Water, salts, and some proteins can be removed by membranes having permeability in the range of conventional microdialysis fibers. All molecules, including large proteins can pass through fibers having the characteristics of conventional ultrafiltration probes.

The removal of substantially only water will increase the crystalloid and colloid osmolarity of the fluid left behind, while the removal of water and salts will increase the colloid osmotic pressure of fluid left behind. Tissue osmolarity will be maintained by the water that is transmitted through the corresponding tissue. Increasing the osmolarity of extracellular fluid, or preventing a decrease in osmolarity, will have the effect of improving convection and diffusion in a tissue. These effects will improve edema removal, and can also be used to advantage for drug delivery. Suitable drugs for delivery in this manner include, for instance, neuroprotectant agents, antimicrobial agents (e.g., antibacterials and antivirals), vasodilators (e.g., nitric oxide), anticoagulants, genetic vectors, and anti-inflammatory agents (e.g., steroids for the treatment of compartment syndrome).

Hollow fibers suitable for use in the present invention provide an optimal combination of other properties as well, such as inner diameter, outer diameter, wall thickness, tensile strength, compressive strength, and transmembrane conductance. Collectively these properties are suitable to provide the fiber with the ability to withstand positive or negative pressure. Transmembrane conductance is a measure of the ability to transmit water and other substances. High transmembrane conductance is seen in large pore fibers.

These fibers can be used singly or can be grouped into bundles, e.g. containing anywhere from a plurality to several hundred or even several thousand such fibers. In most cases, a hollow fiber will be used as a cylindrical membrane in a manner that permits selective exchange of materials across its walls. Optionally, such fibers can be used in varying combinations, such as coaxial fibers having differing permeabilities to oxygen, cells, and fluid or its components. Such combinations can be designed and used to provide a sequential selectivity with respect to fluid flowing sequentially through the fibers or fiber portions. Preferred embodiment as compared to in-situ methods Semipermeable membranes can be prepared in any suitable manner, e.g., by microperforating an otherwise intact capillary or by spinning hollow fiber membranes from natural or synthetic polymers. Such fibers can be formed having any desired characteristics, e.g., isotropic (dense or porous) and anisotropic (asymmetric). Examples of suitable materials for use as microcatheters of this invention include, but are not limited to, microinfusion tubing such as polyethylene tubing available from Clay Adams under the designations PE-10 (0.28 mm/0.61 mm, inner and outer diameters), PE-20 (0.38 mm/1.09 mm), PE-50 (0.58 mm/0.965 mm) and PE-90 (0.86 mm/1.27 mm). Such tubing can be microperforated by any suitable means, such as lasers and the like.

Optionally, and preferably, microcatheters used in this invention can have regions of varying characteristics, including varying porosity, rigidity, and the like, for instance those that vary between sequential and adjacent, or suitably spaced, longitudinal sections, or in or any other suitable pattern. Such variations can be used, for instance, in a size exclusion fashion to improve or provide the ability to retain or permit the passage of solutes of varying sizes in a predetermined manner. Such variations can also be used to provide regions of greater rigidity or varying structure (e.g., fluted), in order facilitate their placement in tissue. Such variations can also include the incorporation of means (e.g., radioopaque materials) to facilitate the visualization of implanted catheters. Such variations can also be used to place regions of semipermeable membranes in desired locations within the tissue, e.g., in order to effect a gradient between two or more regions, or to avoid the placement of semipermeable regions in particular tissues or areas thereof.

When blood or body fluids are treated with extracorporeal circuits, hollow fibers can be used in a sequential manner to improve separation. WRT can be performed first, which will improve separation, when trying to remove certain agents by ultrafiltration or other means. Also, serial flow through hollow fibers or cartridges of various cutoffs can exclude or retain specific ranges of molecules of given molecular weight.

Suitable membranes are available commercially, including from Applied Membrane Technologies, as their line of "AMT" type membranes, and from Minntech, Inc. Examples of suitable membranes, including the materials and available pore sizes and dimensions, are provided in TABLE I.

One or more introducing components are preferably included in a catheter system of this invention and can be provided in any suitable form, e.g., using suitable introducers (typically in the form of one or more sheaths used to facilitate the placement of a catheter through the skin, typically into a vein or artery), guidewires (e.g., typically coiled wires adapted to fit inside a catheter assembly for the purpose of directing the catheter into or through a tissue site), stylets or trocars (e.g., sharp pointed instrument used with a cannula for piercing a vessel or chamber to facilitate insertion of the cannula), and combinations thereof. In turn, the introducing components, including various components, can provide an assembly that is steerable or nonsteerable, useful with open incision or using minimally invasive means, and/or adapted to be dilated, expanded, or compressed, thermally regulated. Optionally, an introducing component can comprise or be provided in the form of a shaped memory alloy, such as Nitinol (NiTi).

The invention will be further described with reference to the Figures, wherein FIGS. 1–4 show a preferred system of the invention for use in treating compartment syndrome, and FIGS. 5–10 show a preferred system of the invention for use in treating cerebral edema.

FIG. 1 shows a catheter assembly 10 that includes an implantable catheter body 12 providing a conduit leading through Y-adaptor 25 to a pressure line and associated connector 14 for attachment to a pressure monitor (not shown), as well as a conduit and associated connector 16 for attachment to a vacuum source (not shown). Within the vacuum conduit, and attached by Y-connectors 24 and 26, are a filtrate collection assembly 18 and filter/cap assembly 28/29, respectively. The collection assembly can take any suitable form, and is here shown as including a syringe collection chamber 21, above which is positioned the proximal end of the incoming portion of collection tube. Also associated with the vacuum conduit is filter/cap assembly 29. With the cap 29 removed, fluid is vented via Y-connector 26 and collected via drip tube 20 and syringe 21.

FIG. 2 shows a cross-section taken across A—A of the catheter assembly 12, showing the outer impermeable tube wall 30 of catheter assembly 12, within which are positioned a central fluid filled tube 32 for pressure measurement, and seven circumferentially placed semipermeable membranes 34.

FIG. 3, in turn, shows an enlarged detailed view of the distal end of catheter assembly 12 as shown in FIG. 1, including the distal portions of semipermeable catheters 34, which are shown terminating within a circumferential collar portion 40 that itself terminates distally in a split end, to prevent constriction by surrounding tissue. In this particular embodiment, the catheters are also closed on their distal ends, within a region of suitable adhesive 44. In the region proximal to collar portion 40, however, the walls of the membranes are accessible for direct contact with surrounding tissue. Also shown is the fluid filled pressure lumen 32, extending distally beyond collar 40 and into the split end 42, in order to provide unimpeded contact with tissue fluid. Adhesive 41 is shown providing a seal between collar 40 and split end 42.

FIG. 4 shows components of introducing components suitable for use with the catheter assembly of FIG. 1, including a trocar needle 50 and split sheath 52. In use, the trocar can be positioned within the sheath, and the combination positioned within the tissue site. Once positioned, the trocar can be removed from the sheath, leaving the sheath in position within the body, whereupon the catheter portion 12 of assembly 10 can be inserted into the sheath. With the catheter positioned, the sheath can be finally removed, leaving the catheter effectively in place within the body. Following use, the catheter assembly can itself be removed from the tissue site, or permitted to remain in place for subsequent use.

In the course of using the system shown in FIGS. 1–4, the vacuum source is operated in order to draw a vacuum through the associated conduit, and ultimately, on the proximal ends of closed membranes 34. In turn, water and permeable solutes are drawn through the membrane walls and into the lumen for removal from the tissue. Simultaneously, the fluid filled, open-ended, central tube can be operated to measure tissue pressure within the split end 42.

Turning briefly to FIGS. 5–10 there is shown a preferred embodiment of a system of the present invention having particular use in the treatment of cerebral edema. FIG. 5 shows a catheter assembly 60 that includes an implantable catheter body 62 that is adapted to be controllably and operably connected (via Y-adaptor 82) with a conduit and associated connector 64 for attachment to a pressure monitor (not shown). The catheter body 62 is also adapted to be controllably and operably connected (via Y-adaptors 82, 74 and 70, sequentially) with a conduit and associated connector 66 for attachment to a vacuum source (not shown). The pressure monitor line provided by conduit 64 further includes a coupling portion 85 near Y-adaptor 82, which is shown in its uncoupled form, to permit the placement of an introducer (e.g., positioning stylet) through the corresponding access aperture 83 and longitudinally down the body of catheter 62.

Attached within the vacuum conduit, via Y-connectors 82 and 74, respectively, are an assembly of components (including stopcock 78, desiccant dryer 80 and an air filter 81) for providing filtered, desiccated air or other suitable gas from a remote source (not shown) to catheter 62. Also attached within the vacuum conduit, via connectors 82, 74 and 70, respectively, are a drip tube 71 and associated syringe collection chamber 72. With stopcock 78 in the open position, air or other suitable gas can be delivered to the catheter distal end positioned within the body.

FIG. 6 shows a cross section taken across A—A of catheter assembly 62, including the outer impermeable tube portion 84 enclosing a central inner tube 86, fluid filled for pressure measurement, and six semipermeable membrane catheters 88, as well as an impermeable tube 90 for the supply of desiccated gas. FIG. 7, by contrast, shows a cross section taken across B—B of the catheter assembly of FIG. 5, and shows the outer wall 92 of the Y-connector 82, enclosing the central inner tube 86 adjacent the desiccated gas supply tube 90. The semipermeable membranes, which are located distally from this point, are open-ended on both ends, in order to permit desiccated gas to be delivered via supply tube 90 to their distal ends, and to then traverse the membranes in a proximal direction toward Y-connector 82, becoming hydrated through the walls of the membranes by surrounding tissue.

The operation of the various parts is depicted in FIG. 8, in which the distal end of catheter portion 62 is shown in enlarged detail, as having a collar portion 96 attaching, distally, a soft distal tip 98 (e.g., in an adhered or press fit connection) and attaching proximally the assembled catheters (including membranes 88, air supply tube 90, inner fluid filled lumen 86). The collar provides an open space 100 (plenum) between the distal tip and catheter assembly, for use as an air return chamber. The distal tip is provided with open pores 102 in order to permit free access of surrounding tissue fluids to the catheter tips. The inner fluid filled lumen extends sufficiently into the distal tip to permit pressure determination to be made there.

Figure 9:
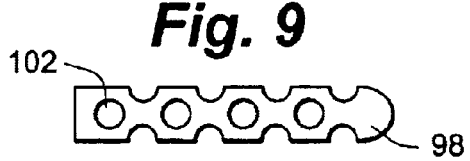
FIG. 9 shows an enlarged detailed view of the soft distal tip of the catheter of FIG. 5.
Figure 10A:
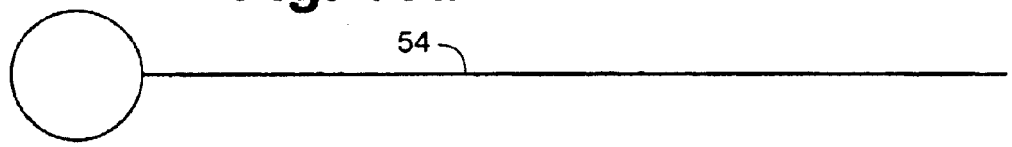
FIG. 10 shows component parts for use in accessing the brain tissue, in order to place the catheter of FIG. 5.
Figure 10B:
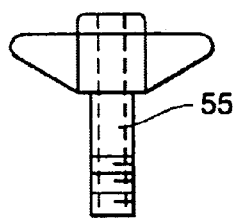
Figure 10C:
Figure 10D:
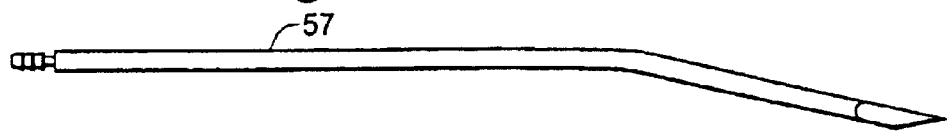

In use, desiccated air (or other suitable gas) is supplied through air supply tube 90 and into the air return chamber, where it circulates in order to enter the open lumen of the semipermeable catheters, and traverse the lumen of those catheters in a proximal direction. With the walls of the membranes in contact with surrounding tissue, the desiccated air can be drawn by the vacuum applied from a proximal direction on the open ended membranes. Simultaneously, the fluid filled inner lumen can be used to determine tissue pressure, by its proximal functional attachment to a suitable pressure measurement device (not shown). As compared to the embodiment of FIGS. 1–4, the membranes of FIGS. 5–10 are open-ended on both ends, to permit the flow of desiccated gas therein. FIG. 9 shows an isolated view of distal tip 98, showing a typical arrangement of access pores 102, while FIG. 10 shows a stylet 104 adapted to be used for assistance in placing the catheter portion 62 of FIG. 5. Optionally, this embodiment can be operated with the stopcock 78 closed to get suction only. As a further optional feature, some (e.g., alternating) fibers can be closed at distal end such that these fibers operate only as suction devices while other fibers have circulating dry air.

FIG. 10 shows an assortment of components adapted for use in preparing the skull and/or positioning a catheter according to FIG. 5. In particular, there is shown a positioning stylet 54 (FIG. 10a), self tapping bolt 55 (FIG. 10b), burr hole drill 56 (FIG. 10c) and tunneling trocar 57 (FIG. 10d). In use, the burr hole drill can be used to provide access through the skull and to the parenchymal tissue beneath. The catheter assembly of this invention can be positioned with the stylet and in the desired location directly, by first securing the bolt into the skull, and positioning the catheter assembly therethrough. Optionally, the catheter assembly can be positioned to a site remote from the access hole, by employing the tunneling trocar 10d beneath the skull as sufficient distance under the scalp, then inserting the catheter assembly therein.

Figure 11:
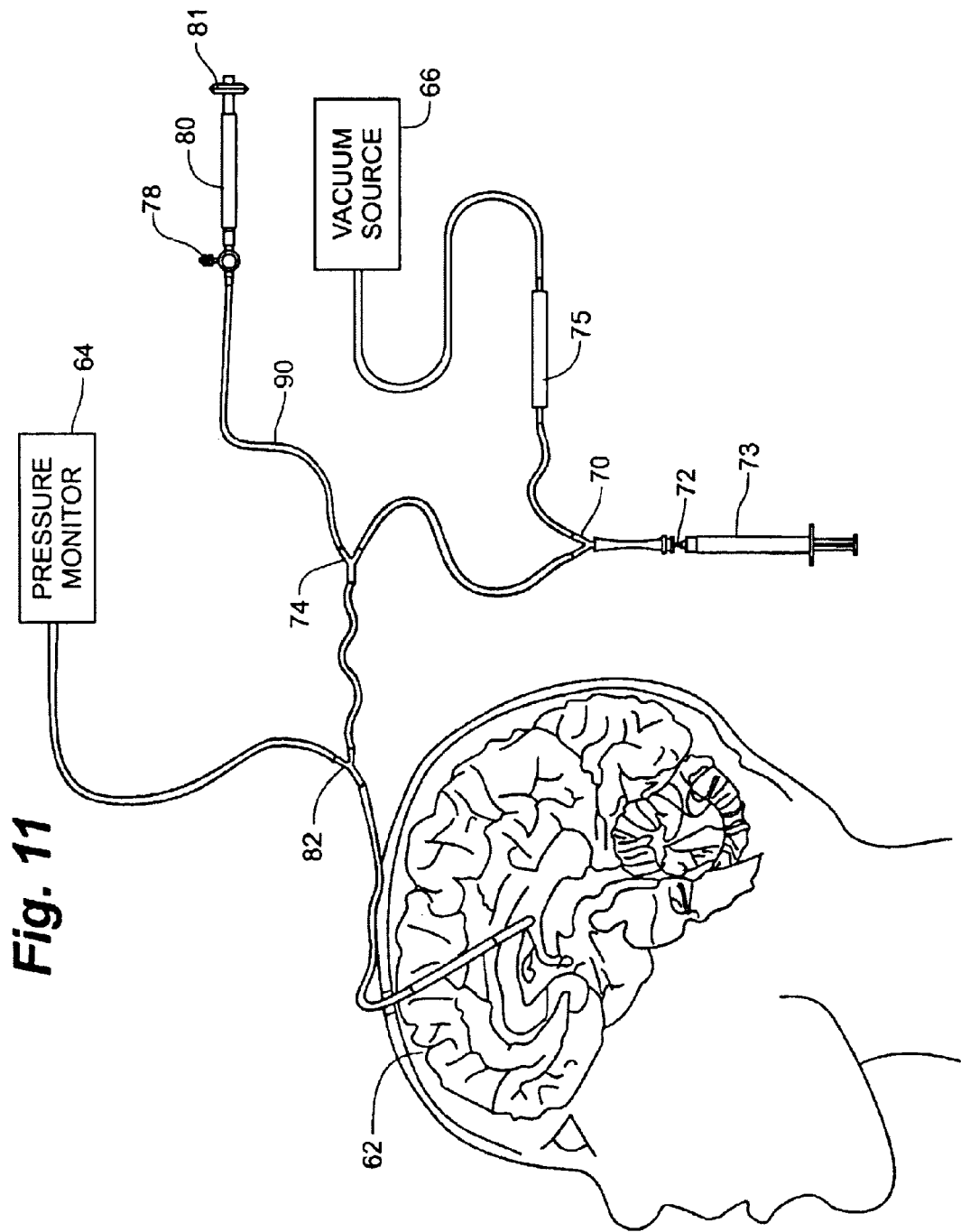
FIG. 11 is a diagram with the catheter shown in position within the brain of a patient.

Finally, FIG. 11 shows a schematic diagram showing the placement and use of a catheter assembly such as that shown in FIG. 5. The catheter is shown positioned within the brain tissue site exhibiting swelling, in a manner that permits the controllable flow of desiccated air from desiccant 80 and through stopcock 78 and into air supply tubes 90 within the catheter body. As the desiccated air travels through air supply tube 90 exiting into the air return chamber at the distal end of the catheter body, where it is drawn into the plurality of open-ended semipermeable membranes. As the desiccated air travels back, proximally, through the membranes, it draws moisture through the exposed portions of those membranes in a manner sufficient to remove water or vapor from the surrounding tissue. Once removed from the body, fluid is drawn toward the collection chamber by vacuum source 66, showing also optional exit desiccant 75, with drip tube 72 providing a suitable trap to permit fluid to be withdrawn from the vacuum line.

As shown in FIGS. 5–11, the preferred system also provides an associated pressure monitor 64 and associated conduits and connectors, which is adapted to be used simultaneously with the delivery and recovery of desiccated gas.

A system such as that shown in FIGS. 1–4 can be used with the following protocol and instructions in order to treat sites at risk for compartment syndrome. Patients considered candidates for prophylactic use of compartment syndrome therapy must meet all of the following criteria: 1) be at risk for compartment syndrome, 2) have a single fracture, 3) have closed or Gustilo grade I open tibial shaft fracture that requires surgical stabilization, 4) are skeletally mature (generally over age 16), 5) have no other traumatic injury, and 6) be mentally alert and able to sign patient consent form.

Patients not considered candidates for compartment syndrome therapy include the following: 1) have fracture currently or previously treated by closed methods (casting, bracing, or splinting), 2) have grade II or grade III open fractures, 3) have evidence of CS at the time of admission, 4) are greater than 80 years of age, 5) have medical condition(s) which preclude use of indwelling catheters for up to 48 hours, and 6) have co-morbidities that may increase the incidence of compartment syndrome (shock, major abdominal or thoracic trauma, massive soft tissue trauma).

Certain cautions will typically be followed with regard to the use of such a system, including:

1. Care should be taken when inserting the introducer to avoid any nerves or large blood vessels in vicinity of treatment site.

2. Slit tubing tip and hollow fiber bundle are fragile. Care should be taken when inserting catheter into sheath. Damage to the tip may lead to false pressure readings.

3. If the catheter is not located in desired location, remove the catheter and reinsert the introducer to reposition the catheter at new location.

4. To ensure accurate pressure reading, the pressure monitor's transducer diaphragm must be positioned at same height as the tip of the catheter.

Figure 12:
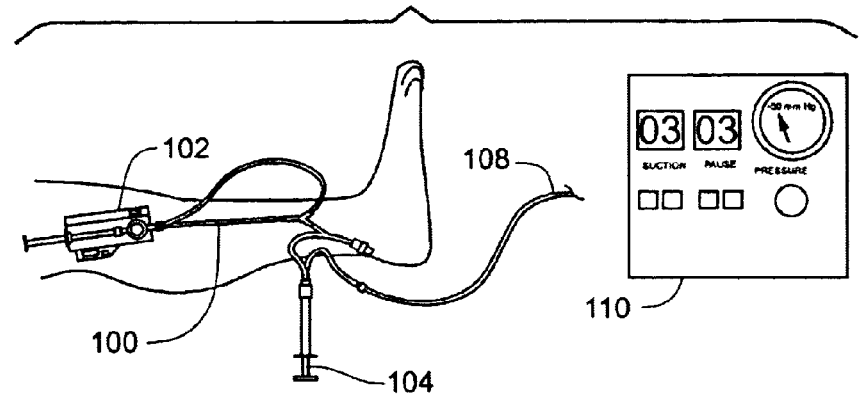
FIGS. 12–21 provide various views and steps arising in the use of a system such as that shown in FIGS. 1–4.
Figure 13:
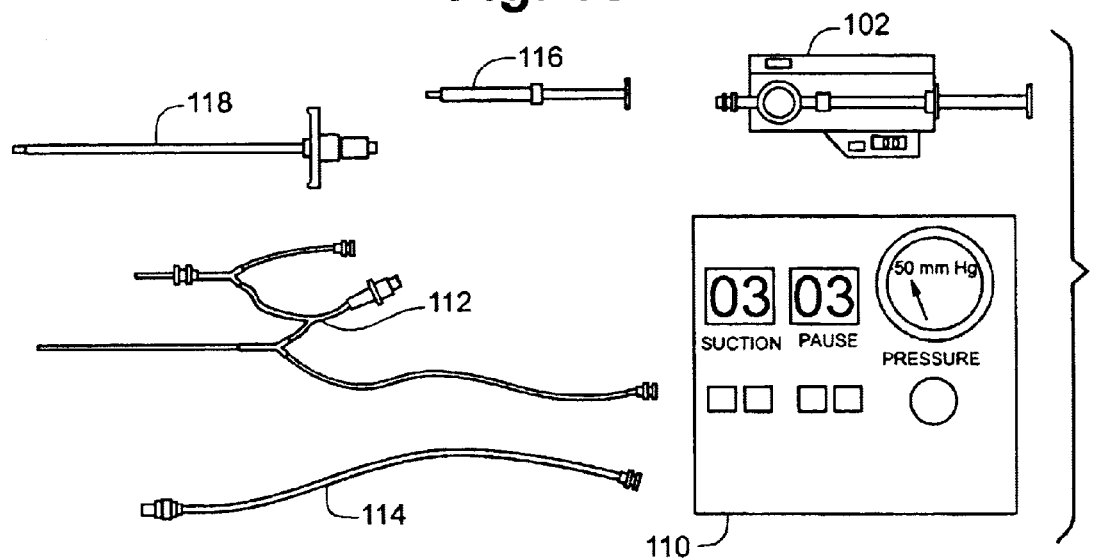

The system is designed to remove interstitial fluid from body muscle compartments while simultaneously monitoring compartment pressure. The goal is to reduce the severity of compartment syndrome by reducing fluid volume while monitoring tissue pressure within the affected muscle compartment. A preferred system and related components is shown in FIGS. 12 and 13, showing the functional arrangement of a CST catheter 100 inserted into a compartment, and including a pressure monitor 102, fluid collection reservoir 104 and vent 106, as well as a line 108 to an intermittent vacuum pump 110. Various components making up a preferred system of this type are shown in FIG. 13 as including the CST catheter set 112 and tubing extension set 114, as well as a 3 cc syringe with cap 116 and introducer 118.

To place the catheter, an introducer, consisting of a Teflon™ sheath over a stainless steel trocar, is initially inserted into the muscle compartment at the site of therapy. After the introducer is positioned, the stainless steel trocar is used as a radio-opaque marker to fluoroscopically verify sheath position. After position is verified, the trocar is removed and the catheter is then inserted through the open sheath lumen. The sheath is then longitudinally split and separated for removal, allowing the catheter to be in intimate contact with the surrounding tissue. The catheter is designed to be in-dwelling for up to 24 hours.

The catheter, in combination with a suitable pressure monitor (e.g., shown here as a Stryker Intra-Compartment Pressure Monitor), can measure the intramuscular pressure during therapy. Optionally, the system can include continuous injection, provided by a syringe pump, in combination with disposable pressure sensors (as currently used for arterial blood pressure measurement) that are adapted to be plugged into standard hospital pressure monitors. To measure this pressure, the catheter's distal tip employs a slit tube to ensure fluid communication with the surrounding tissue. Applicant has discovered the manner in which conventional pressure monitoring systems can be modified so as to permit the infusion of on the order of one to fifty microliters per hour of saline into the fluid column to maintain patency and accuracy.

The catheter has a bundle of seven (7) filtration fibers located near its distal tip. A vacuum pressure of negative 50 mm Hg is applied intermittently to remove interstitial fluid in the vicinity of the catheter. The vacuum pressure "On" and "Off" time is set at (3) three minutes on and (3) three minutes off. After removal, the fluid is collected in a graduated 3 cc syringe with a female luer distal end. Optionally, both the vacuum applied and the timing of vacuum can be adjusted as desired. For instance, such vacuum pressure can be used at between about −1 to about −760 mm Hg, and more preferably between about −50 to about −500 mm Hg. The vacuum pressure can be cycled so as to provide "On" and "Off" cycles at periodic time intervals (e.g., from a few seconds to on the order of 30 minutes "on", followed independently by a few seconds to on the order of 30 minutes off. After removal, the fluid is collected in a graduated 3 cc syringe with a male luer on the distal end.

The system can be provided in the form of one or more individually packaged sterile sets, including an introducer and catheter set, that can be used in combination with one or more other components commercially available in order to provide a compartment syndrome therapy ("CST") system of this invention (e.g., a pressure monitor with associated disposable components, a vacuum pump (e.g., Medela brand), a syringe with cap, and an extension tubing set.

Figure 14:
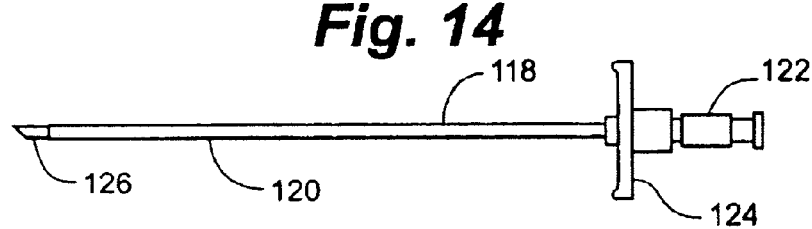

The introducer provides access into the muscle compartment for placement of the CST catheter. As shown, the set consists of a 5 French tear-away sheath placed over a mating stainless steel trocar. After placement and optional x-ray verification, the trocar is removed, the catheter is inserted, and then the sheath's hub and shaft are split longitudinally and removed from the in-dwelling CST catheter. The CST introducer 118 is illustrated in FIG. 14.

The tear-away sheath 120 is composed of a thin-walled plastic tube sized to allow introduction of the 5 French CST catheter. Both the hub 122 and sheath 124 are designed to be longitudinally split for easy removal around the in-dwelling CST catheter. The mating trocar 126 is composed of 304 stainless steel. Its three-(3) facet tip is electro-polished to a sharp point.

The CST catheter set is designed to remove excess interstitial fluid buildup and simultaneously monitor compartment pressure. One or more catheter sets can be used, of the same or different types and in varying positions during the course of treatment. The catheter portion of the set is 5 French in diameter and contains a bundle of seven (7) porous hollow fibers near its distal tip. The fibers remove the surrounding interstitial fluid through both passive drainage and active vacuum. The fluid is collected in a fluid trap located in-line with the vacuum source. The fluid collection port is connected to a 3 cc syringe. A filtered vent is connected to the vacuum line to relieve vacuum when desired.

Figure 15:
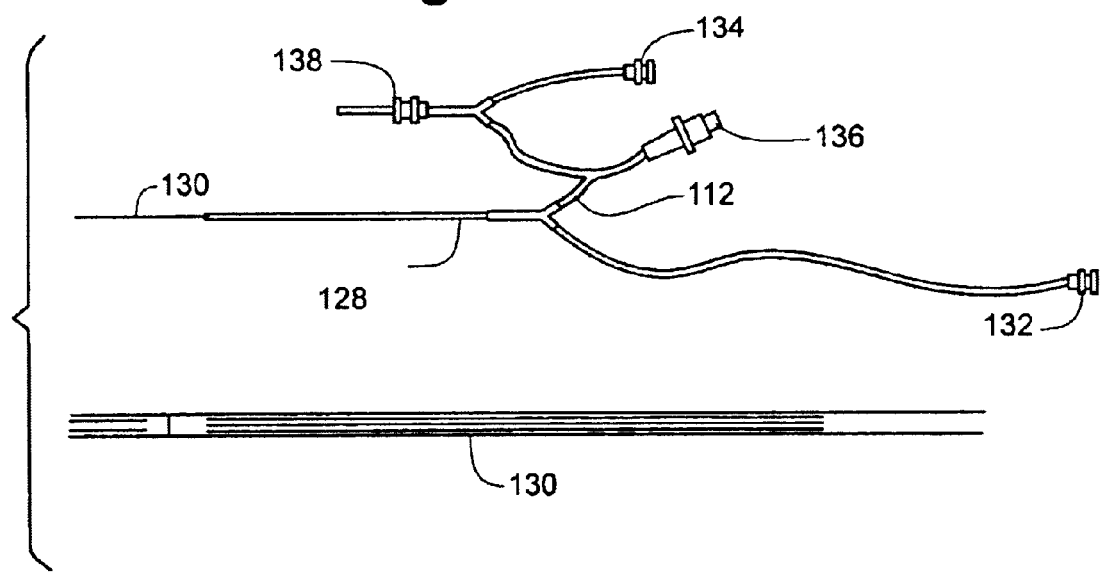

With the vacuum source turned on or off, the catheter supports compartment pressure monitoring by providing a fluid column from the tissue through the slit lumen at the catheter's tip to the external Stryker pressure transducer. FIG. 15 is a drawing of the CST catheter set 112 with its major components identified and a detail drawing of the catheter's tip section.

The catheter body 128 can be composed, for instance, of two coaxial polyimide tubes affixed independently to each of the two Y connector ports, or more preferably, a polyimide outer tube and a stainless steel inner lumen tube to give the catheter more stiffness. The outer tubing is connected to the fibers and is used for fluid drainage. It is fiber reinforced to minimize kinking. The inner tubing is the pressure monitoring lumen. At its distal tip, the inner tubing extends beyond the outer tubing to support the slit tip and ensure fluid communication with the tissue.

Near the distal end of the catheter is a bundle of seven (7) hollow fibers 130. The fibers are porous hollow filters that pass water and interstitial fluid. The active vacuum is applied to the inside lumen of the filters. The fluid is drawn from the surrounding tissue, through the fibers, out the vacuum lumen and into the fluid collection syringe.

The pressure monitoring line 132 is connected to the inner tubing. The female luer at its proximal end is connected to a Stryker Pressure Monitoring device. The line is fluid filled to maintain communication with the Stryker device. The Stryker Intra-Compartmental Pressure Monitor System is indicated for use on compartment syndrome. Stryker Instruments (Kalamazoo, Mich.), Pressure Monitor (part #295-1), quick pressure monitor set (part #295-2), normal saline syringe (3 cc NaCl Fill/Syringe, part #295-5), and quick pressure monitor pack (part #295-2, including side ported needle, 18 ga.×2.5 inch and diaphragm chamber.)

The vacuum line 134 is connected to the catheter's outer tubing. The female luer at its proximal end is connected to the vacuum pump. A vent 136 with a 0.2-micron filter is attached to the vacuum line. The vent is normally closed and can be opened to relieve vacuum pressure by removing the attached cap. The fluid collection line is connected to the vacuum line. The female luer at its proximal end along with the protruding drip tube 138 are inserted into a 3 cc syringe acting as a sample collection reservoir. Sterile 3 cc syringe with cap (Becton Dickinson, Franklin Lakes, N.J.), part #B-D, 3 ml Luer-Lok™ syringe.

Figure 16:
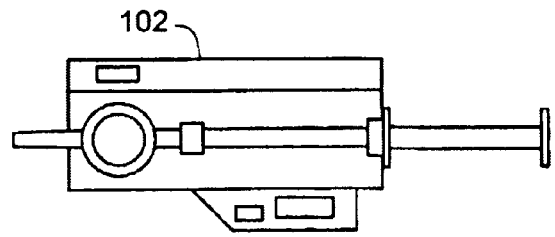

The Stryker Intra-Compartment Pressure Monitor is a hand-held, portable pressure monitor specifically designed to measure intramuscular pressures. A complete description of the device and its associated disposables, the diaphragm chamber and saline filled syringe, are described in its instruction for use provided by Stryker. See the monitor 102 in FIG. 16, in the form of a Stryker Pressure Monitor, Model 295-1 with disposable diaphragm chamber and syringe.

The vacuum pump is used to control the vacuum pressure, the "suction" interval, and the "pause" interval. The pump is connected to the catheter set's vacuum line. A suitable pump is manufactured by Medela, Inc. (McHenry, Ill.) as model 046. The Medela Pump meets Class IIa medical product basic requirements in accordance with Appendix 1 of the Council Directive 93/42/EEC Governing medical products. Pump Setting Ranges:

| Vacuum Pressure | 0–55 mm Hg |
| Suction Time | 0–99 minutes in 1 minute steps |
| Pause Time | 0–99 minutes in 1 minute steps |

A standard sterile 3 cc syringe with a female luer fitting is used as the fluid reservoir. It can be easily attached to the catheter set's fluid collection port. A standard sterile extension tubing set is used to connect the vacuum line to the vacuum source, e.g., as available from Medex (Dublin, Ohio), as part ## 536040 (60 in/152 cm Mini Vol. Ext. APV 0.3 ml). Specific length is dependent on the pump location. The tubing set is supplied sterile in a pouch. It comes with one male and one female luer connector with protective caps.

Prepare catheter for placement following standard wound care practice. Connect the syringe to the catheter's fluid collection port. Set the syringe plunger to approximately the 2 cc graduation, and connect the sterile 3 cc syringe to the fluid collection port. Connect the catheter to the transducer, following instructions provided by the manufacturer. Connect the pressure monitoring line to the pressure monitoring device. Prime the pressure monitoring line, leaving the CST catheter's protective cover in place until the catheter is ready for implantation.

Figure 17:
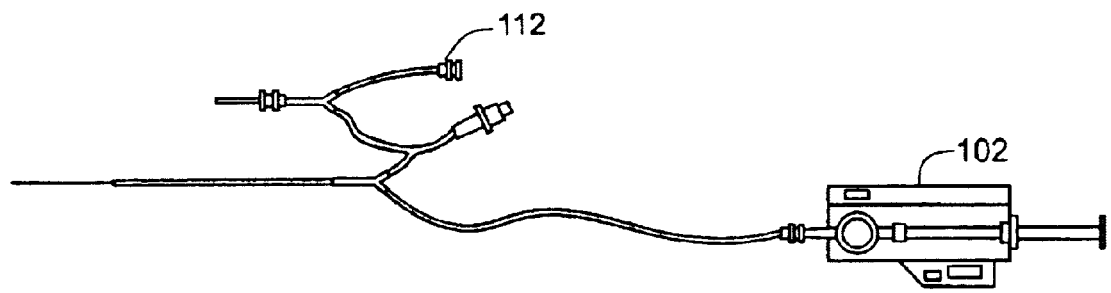

When connected, hold the catheter above the monitor pointing the catheter's distal tip up from horizontal at a 45-degree angle. Slowly flush fluid from the Stryker syringe until a steady stream of fluid is observed flowing from the catheter. FIG. 17 provides a diagram for the connection of the syringe and pressure line priming using the assembly 112 and pressure monitor 102.

Set vacuum pump PRESSURE, SUCTION Interval, and PAUSE Interval (reference vacuum pump instruction for use provided by the manufacturer.)

1. Set vacuum pump pressure. Adjust the pump's pressure control knob to −50 mm Hg+/−5 mm Hg.

2. Set SUCTION Interval. Adjust the pump's "Suction Time" to 03 minutes.

Figure 18:
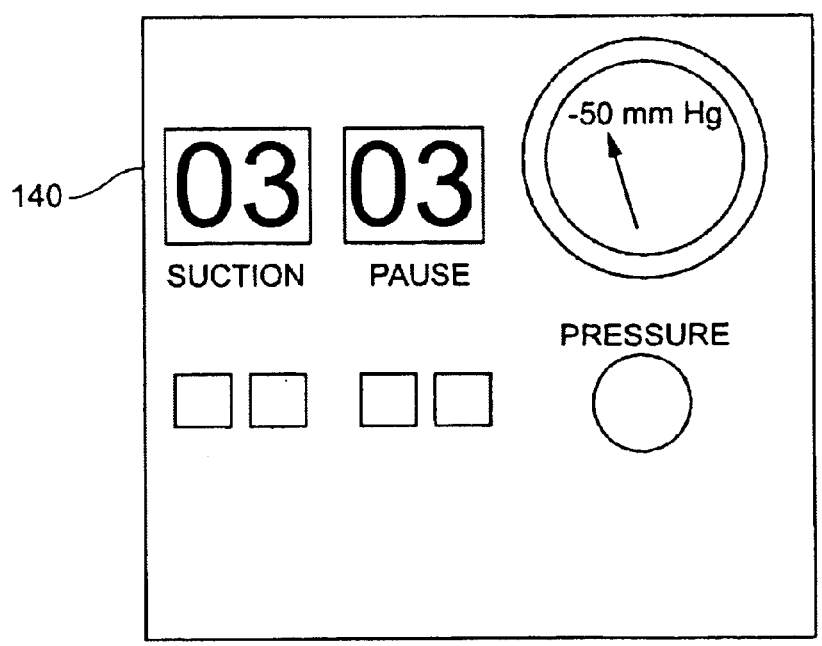

3. Set PAUSE Interval. Adjust the pump's "Pause Time" to 03 minutes. (See FIG. 18 for pump settings 140).

4. Monitor pump parameters. Throughout treatment, monitor the pump settings to ensure pump is working and that unauthorized or accidental changes in pump parameters have not occurred.

Figure 19:
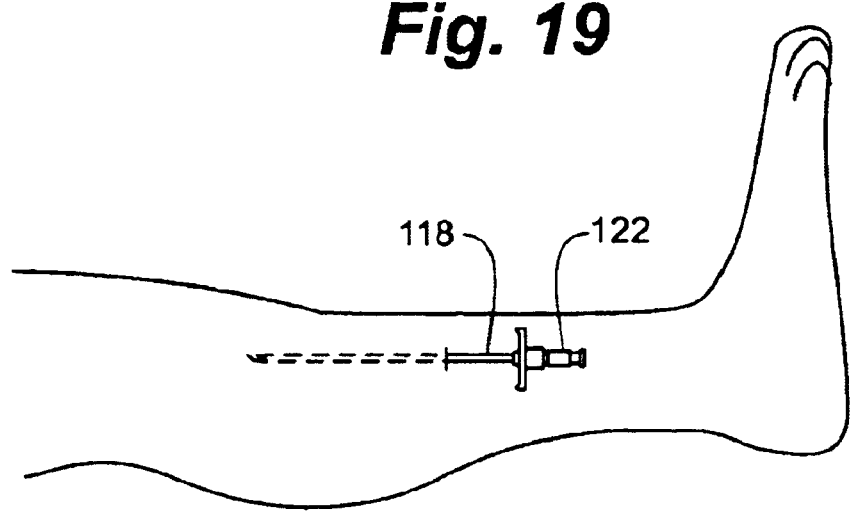
Figure 20:
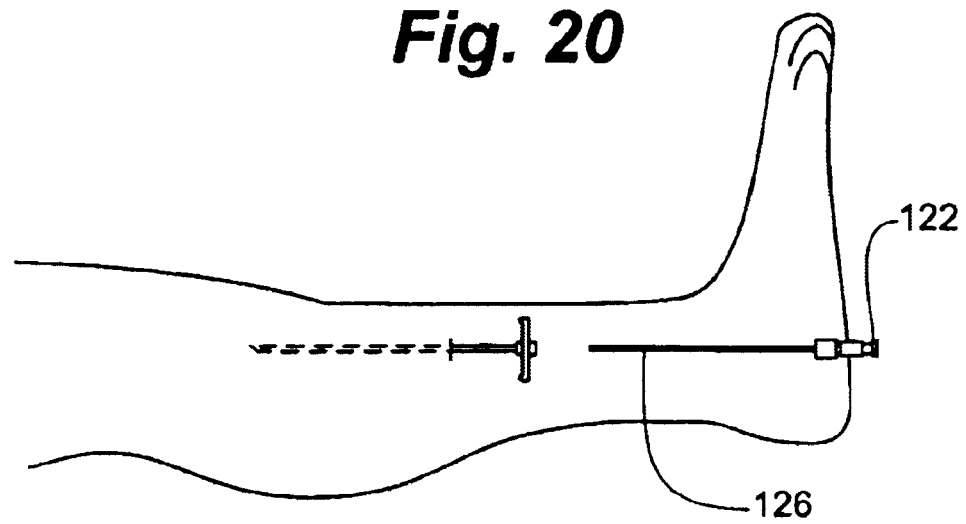

Insert the introducer into the muscle compartment. Prepare the skin surface at point of insertion using standard antiseptic methods. Remove the introducer's protective cover and insert the introducer into the site of therapy. Avoid excessive bending or manipulation of the introducer during insertion to minimize distortion of sheath when the trocar is removed. (See FIG. 19). Care should be taken when inserting introducer to avoid any nerves or large blood vessels in vicinity of treatment site. If considered necessary, verify the introducer position using fluoroscopy or other suitable means. Remove the trocar by slowly twisting the trocar hub to disengage from the sheath hub and then gently removing the trocar 126 and disposing of according to normal procedures. (See FIG. 20).

Insert the catheter by removing and disposing of the protective cover from the catheter. Carefully insert the catheter's tip into the sheath hub. Care should be taken during insertion to ensure that the slit tubing at the catheter's tip is not damaged or distorted. Continue inserting the catheter into the sheath until the silicone tubing on the catheter touches the sheath hub. This will place the distal tip of the catheter approximately 2 to 3 mm from the distal end of the sheath. Since the slit tubing tip and hollow fiber bundle are fragile, care should be taken when inserting the catheter into the sheath.

Figure 21A:
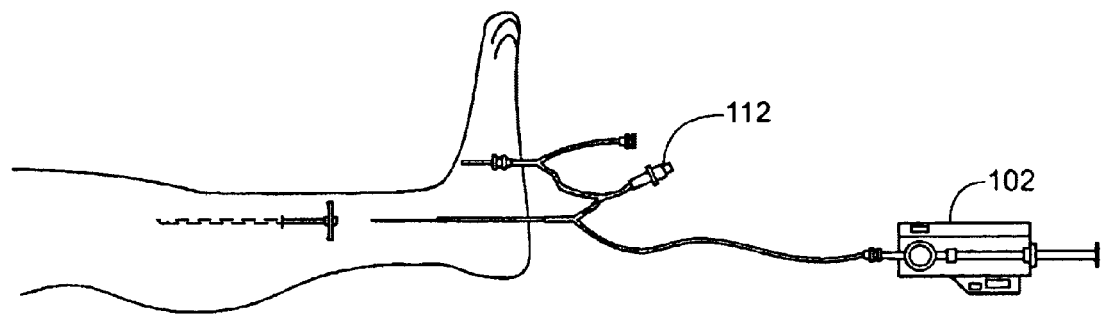
Figure 21B:
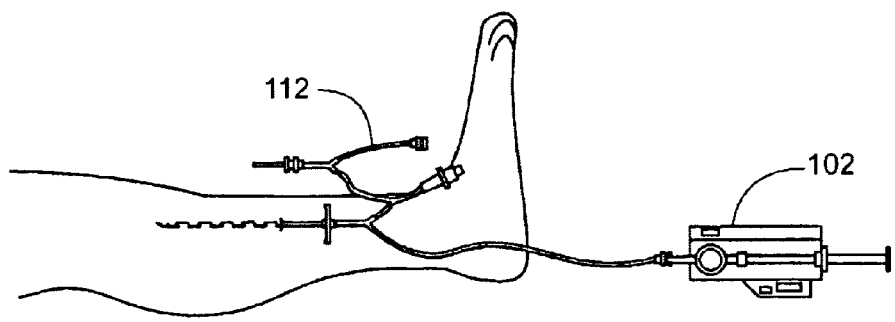

Remove the tear-away sheath. With the catheter in desired position, gently break the sheath hub and begin pulling the sheath out. As the sheath is removed, continue to tear apart the sheath while holding the catheter in place. Two people may be necessary to ensure a steady catheter position during sheath removal. Dispose of the separated sheath using standard practice. (See FIG. 21). If the catheter is not located in desired location, remove the catheter and reinsert the introducer to reposition the catheter at new location.

Maintain the indwelling catheter, using typical standard of care for indwelling catheters at the catheter entrance site. Stabilize the catheter shaft to prevent excessive bending which could kink catheter. After visually confirming that the catheter has been properly placed, position the silicone tubing to prevent kicking.

Position the pressure monitor and syringe reservoir. Position the pressure monitor according to instructions included with monitor. Position the syringe with plunger handle pointing down and near the insertion site, and affix to the body using tape. To ensure accurate pressure reading, the pressure monitor's transducer diaphragm must be positioned at same height as the tip of the catheter.

Connect the vacuum line by connecting the vacuum extension line to the male luer connector on the catheter vacuum line. Next connect the vacuum extension line to the vacuum pump connector. Prime the connecting line with saline. Pressure can be monitored at any time. To ensure patency, inject less than 3/10 cc of saline into the compartment. Refer to the Stryker Instructions for Use. Record the pressure reading, waiting for the display to reach equilibrium. At the doctor's discretion record the pressure reading at timed intervals.

Remove interstitial fluid by turning on the pump and verifying that the vent cap is attached. Continue therapy for a desired period of time (e.g., up to 72 hrs). Continue therapy until muscle compartment pressure is stabilized at acceptable level. During the course of therapy, monitor the fluid drip rate into the syringe reservoir. Remove and replace the syringe whenever 1 to 2 ml of fluid is collected.

Remove and replace the syringe by opening the vent and removing the cap from the vent portion to release vacuum. Aspirate the vacuum line by pulling back the syringe plunger to remove fluid lying in tubing between the vent and syringe. Remove and cap the syringe for analysis of its contents. Immediately attach a new sterile 3 cc syringe and replace the vent cap to continue fluid removal.

Remove the catheter by gently pulling straight back. Set aside and allow vacuum to continue draining. If any resistance is met when retracting the catheter, inject up to ½ ml of saline and attempt removal again. If resistance is still met, leave the device in place for 30 minutes without vacuum, and attempt removal again. Clean the puncture site and apply dressing according to standard procedures, continue standard puncture wound therapy at the therapy site. Dispose of the catheter set using standard practice.

A system such as that shown in FIGS. 5–11 can be used with the following protocol and instructions in order to treat sites at risk for cerebral edema. Prepare the catheter and system by opening the associated packaging while maintaining sterility. The catheter can be placed intracranially by several options at the discretion of the clinician using components found in FIG. 10. Determine the desired site of therapy. The catheter can be placed directly into brain parenchyma with the pressure-monitoring tip placed within the cerebral ventricles.

Position the pressure line and monitor according to instructions. Caution: To ensure accurate pressure reading, ensure that the pressure monitor's transducer diaphragm is positioned at same height as the tip of the catheter. Connect the vacuum line by attaching the vacuum extension line to the catheter vacuum line. Connect the vacuum extension line to the vacuum pump connector. An optional fluid trap including syringe collection chamber and desiccant cartridge may be included in the vacuum line to measure fluid removal. In conditions of high humidity, an optional air desiccator can be used. Remove the air filter from the air intake line and attached the desiccant cartridge using sterile technique. Replace the air filter on the intake of the desiccant cartridge.

A. Monitor Intracranial Pressure
 1) Pressure can be monitored at any time.
 2) Record Pressure Reading. Wait for the display to reach equilibrium. Record the pressure reading at the appropriate intervals.
B. Remove Edema Fluid
 1) Turn on pump or other vacuum source. Confirm flow of air through the air intake.
 2) Monitor fluid collection. During the course of therapy, fluid may accumulate in the syringe and desiccant. Remove the fluid in syringe or replace desiccant when necessary.
 3) Replace optional air intake desiccant cartridge as necessary.
C. Termination of Treatment Clinicians will determine the appropriate time for termination of treatment based on severity of injury and response to treatment. Remove the catheter assembly by gently removing the catheter by pulling straight back. Set aside and allow vacuum to continue draining.

Figure 24:
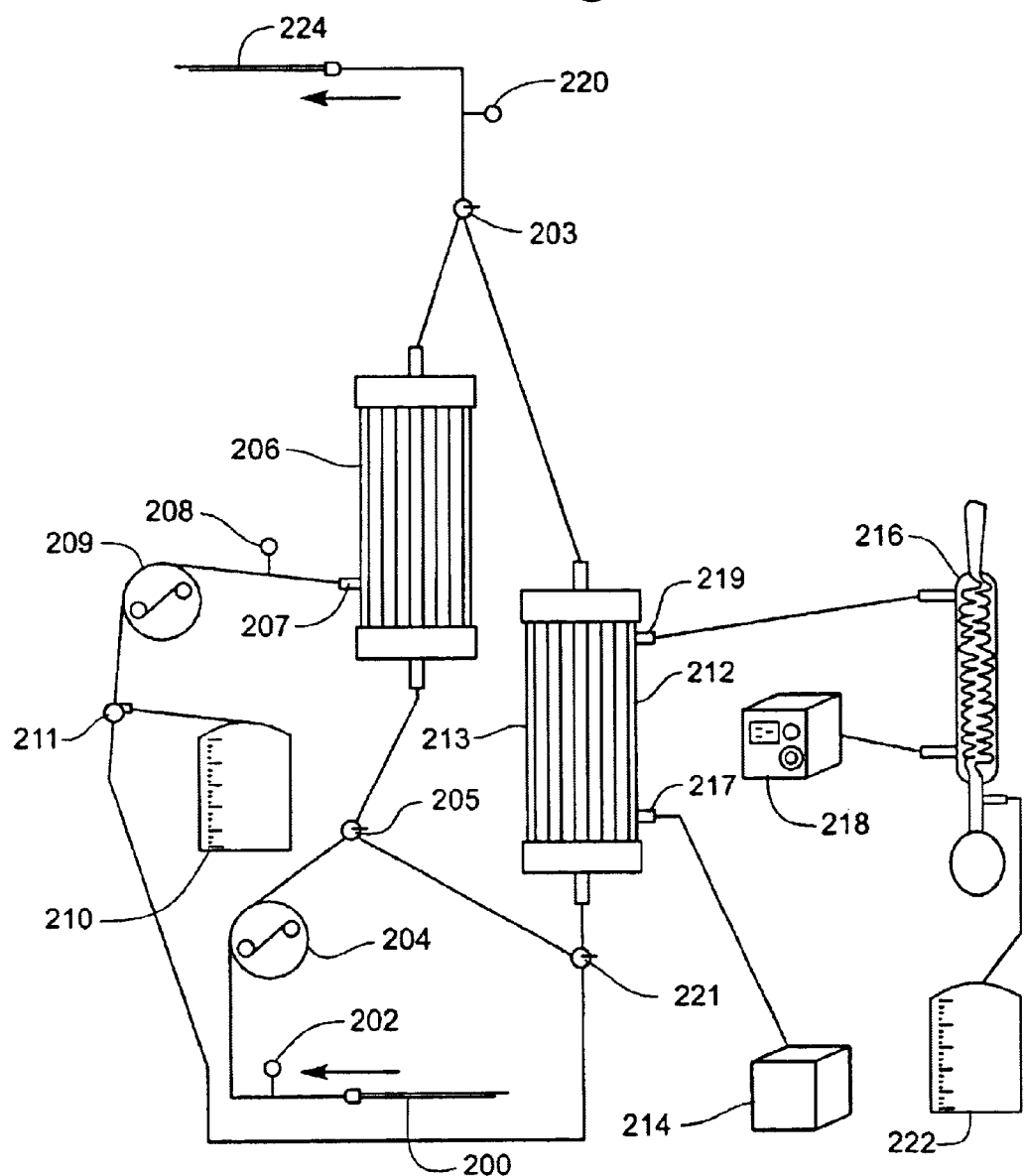
FIGS. 24–26 show alternative schematic diagrams of the use of ultrafiltration in combination with water removal therapy.
Figure 25:
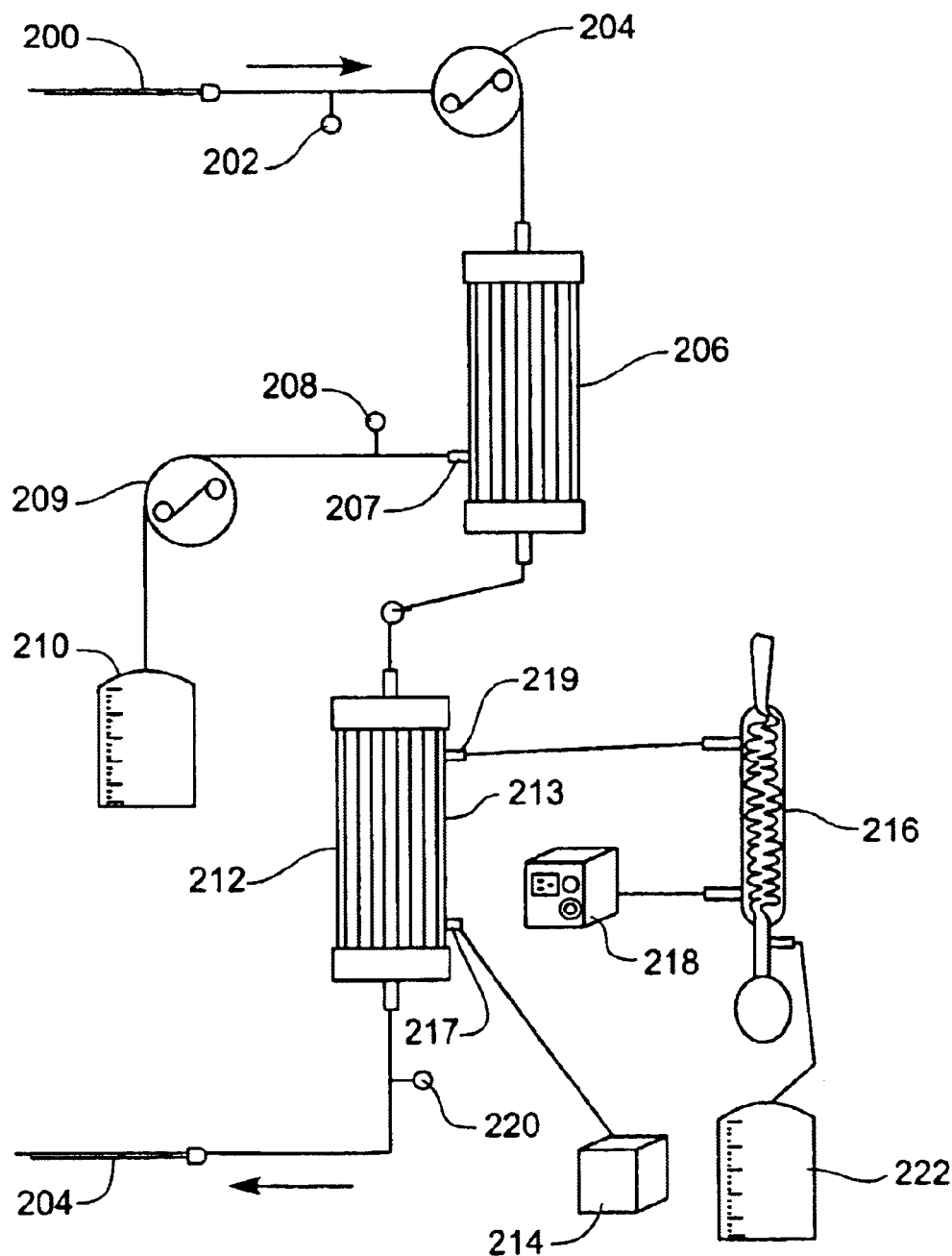
Figure 26:
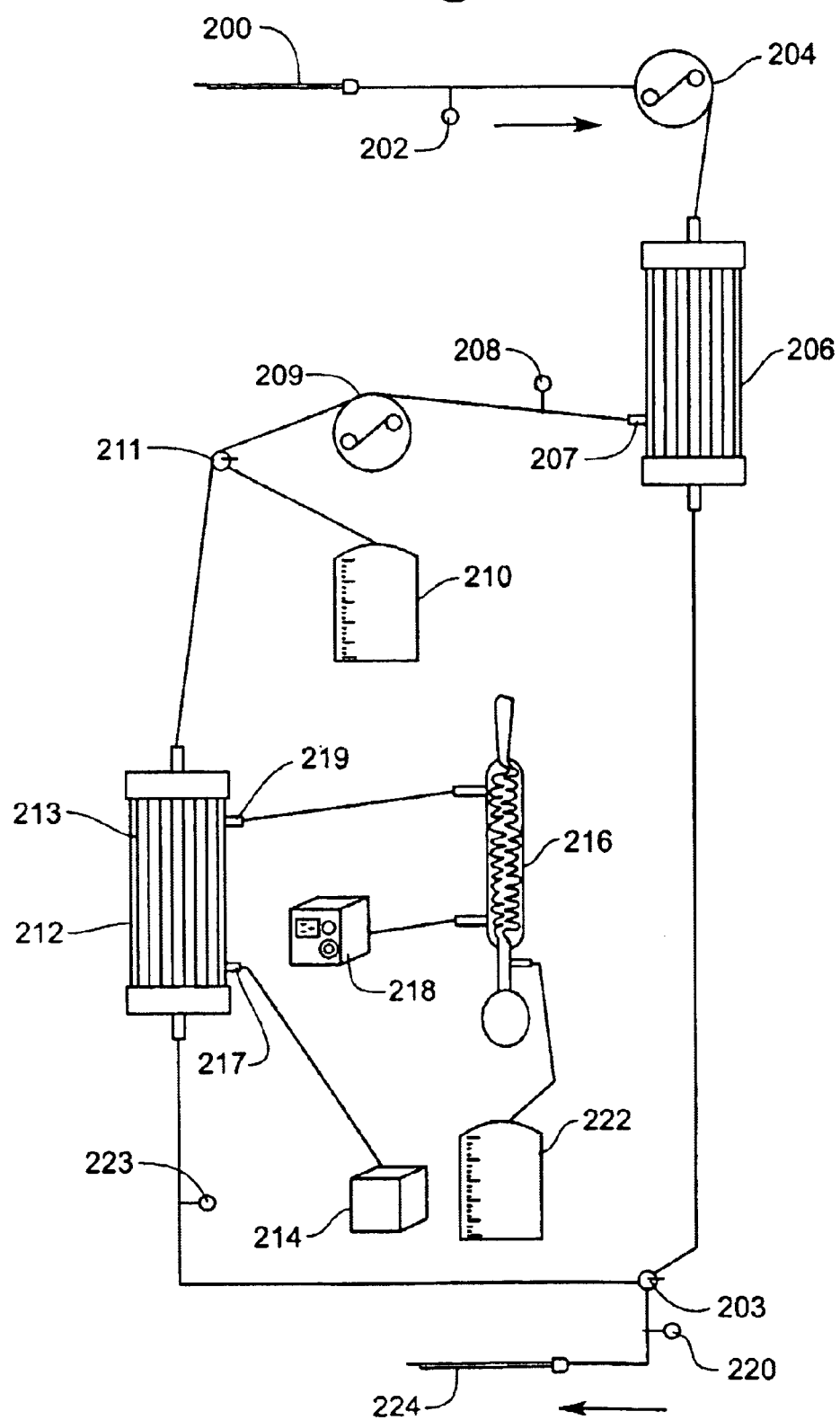

FIGS. 24–26 show various alternative embodiments of systems that employ WRT and ultrafiltration in the manner presently described and claimed.

| UF WRT | Series | Blood/Gas | Gas/Blood | FIG. 25 |
| UF WRT | Parallel | Blood/Gas | Gas/Blood | FIG. 24 |
| UF WRT | Stepped | Air | Ultrafiltrate | FIG. 26 alternative |
| UF WRT | Stepped | Ultrafiltrate | Air | FIG. 26 as shown |
| UF WRT | counterflow | Air | Ultrafiltrate | |

Ultrafiltration cartridge 206 is shown as a hollow fiber cartridge that allows blood flow through the lumen of the hollow fibers. Ultrafiltrate flows across the hollow fiber walls and out the cartridge sideport under negative pressure. Ultrafiltration pressure sensor 208 measures the flow pressure of the ultrafiltrate draining from the ultrafiltration cartridge, while ultrafiltration waste collection bag 210 collects the ultrafiltrate draining out of the ultrafiltration cartridge.

WRT cartridge 212 is also provided in the form of a hollow fiber cartridge that allows blood flow through the lumen of the fibers, while the WRT dry air technology removes water transluminally from the blood. Water vapor is removed from the cartridge through a side port. A dry air source will be attached to one side port while the vacuum is pulled through the condenser which is in turn attached to the other side port. Both the UF cartridge and WRT cartridge can be provided in the form of an elongate housing defining a central axis; the housing containing a plurality of elongate hollow fibers each positioned within the housing substantially parallel to the central axis and defining an extrafilamentary space within the housing, each of the hollow fibers being formed of a material which allows molecular transport therethrough.

Generally, vacuum is used to pull gas through the WRT cartridge. Vacuum is limited in pressure magnitude, but eliminates the possibility of air entering the fluid space. Positive pressure gas can further increase airflow, and if used with hollow fibers without pores-increase flow, especially with no-pore fibers The cartridge generally further provides one or more fiber inlet ports and one or more fiber outlet ports, the ports communicating through the hollow fibers to define corresponding intraluminal fiber flow paths. The cartridge generally also provides one or more housing inlet and outlet ports, the housing ports communicating through the extraluminal space to define an extraluminal flow path, the extraluminal flow path being isolated from the intraluminal flow path such that a material in one path may enter the other path only by molecular transport through the material comprising the hollow fibers.

Those skilled in the art, given the present description, will appreciate the manner in which water vaporization can depend on several factors, including airflow velocity and temperature dependence. Water vapor pressure is directly dependant upon temperature. The key to removal of water with this method is to sweep the water vapor from the lumen of the semipermeable membrane by high velocity airflow.

Water vapor pressure at room temperature is 17 mmHg, while at body temperature it is 47 mmHg. Higher vapor pressure increases mass transport of water. The selection of hollow fiber material can depend upon the molecular species to be removed and/or to be retained. Typically selection is made of a suitable pore size corresponding to the size of the molecules, and particularly biomolecules, keeping in mind the manner in which molecular charge, shape, and other factors can play a role as well, under the particular conditions of use. Generally, water, salts, and/or proteins are targets for removal using a system of this invention, while cells and tissue segments are retained.

Those skilled in the art, given the present description, will appreciate the manner in which a variety of other system components and operating conditions can affect WRT system performance and operation.

With regard to water vaporization efficiency, for instance, it is desirable to obtain the maximum water transport across a per unit area of membrane to minimize cost, minimize blood prime volume and to minimize the amount of air flow, which together will tend to reduce the size of the air handling components as well as the operating costs. Those skilled in the art, given the present description, will appreciate the manner in which various elements can play a role in obtaining the highest water vaporization efficiency, including uniform fluid flow.

One means of improving water vaporization efficiency is to provide uniform air and blood fluid flow within the cartridge housing the membrane elements. Instances of a poor distribution create dead spots where water is not transported through the membrane and lowers the vaporization efficiency. Mass transfer using packed hollow fibers is very efficient, and optimal efficiency is achieved with uniform flow from across the length and cross sectional area of the cartridge. Fluid can be passed through the lumen and gas flowing externally, alternately, gas can be passed through the lumen of the hollow fibers and the fluid can be passed outside the hollow fiber but within the shell of the cartridge.

Improved water vaporization efficiency can also be achieved with low humidity air entering the cartridge, since this allows more water to become vapor up until air saturation is achieved. Means of lowering humidity include passing air through an evaporative condenser, desiccant, hollow fiber air dryer or through a mechanical resistor, or using a compressed gas source.

Further, both vapor pressure and the heat of vaporization can impact performance. It is desirable to have a high vapor pressure for the fluid entering the membrane cartridge in order to obtain maximum water flux efficiency. Vapor pressure is the pressure exerted by a gas (in this case, water vapor) that is in contact with its fluid state. The higher the water vapor pressure, the greater the amount of water vapor present that can be removed. Vapor pressure can be increased by increasing the temperature of the fluids entering the cartridge.

Water vaporization is accompanied by drops in temperature due to the latent heat required for vaporization. Levels of vaporization can be regulated by adjusting cartridge airflow and/or fluid temperatures. Blood flow rates can range from about 10 ml/min to about 500 ml/min, with a preferred range of from about 20 ml/min to about 200 ml/min. Other means to counter the temperature drop due to vaporization can be provided by including impervious tubes in the membrane cartridge that contain a circulating warm fluid such as air or water. Yet other means include the placement of wires in the cartridge that can be heated resistively by electricity.

In the course of performing WRT, it is desirable that the blood gases remain within normal limits. Depending on the composition of the circulating air, the oxygen and carbon dioxide levels can be altered by the water vaporization system. Standard means of controlling blood gases within physiologic limits as used in blood oxygenation for heart lung machines can be applied to WRT systems. These means include oxygenation of blood prior to reintroducing into subject using standard blood gas oxygenators.

Controls systems can impact performance as well, e.g., in order to avoid removing fluid from blood so quickly as to result in hypotension. There are number of means to avoid this including the measurement of hematocrit over time as provided in equipment marketed by HemaMetrics (Crit-Line), Gish (StatSat), Medtronic (BioTrend) and Terumo (CDI 100). Electrolytes measurements can be used to stop, start and control the system operation, as can various other physiologic limits. In line sensors and analytic instruments can be used to measure electrolyte concentrations, with automated controls and fail safe mechanisms employed as desired. Electrical conductivity can also be monitored, in order to determine concentrations in effluent or various other points within a flow path.

A desirable system control parameter will be water removal rates. Utilizing air humidity at the inlet very close to 0%, the fluid collected as the air exits the cartridge will encompass the fluid removed from blood. Like the components used to lower humidity of the air entering the cartridge, these same devices can be used to remove water removed by WRT. The water removed by WRT can be measured by mass or volumetrically. Temperature differences of the blood entering and exiting the cartridge correlates with magnitude of water vaporization and can be used to indicate rates of water loss. Preliminary studies have shown greater hemodynamic stability is obtained with fluid removal rates of about 100 ml per hour.

As also shown in FIGS. 24–26, dry air source 214 will generally be provided in any suitable form as a source of dry air which is pulled through the housing of the cartridge (via one side port) to create vaporization of fluid within the counter current (or optionally, concurrent) flow of blood, e.g. hospital supplied air, desiccant dried air, or a commercial air drier. Condenser 216, in turn, is an apparatus which will be used to condense the water vapor removed from the blood. Vacuum pump 218 will be used to pull a vacuum through the condenser and in turn the WRT cartridge from the other side port of the cartridge housing. This will pull dry air through the housing and across the surface of the hollow fibers, removing water from the blood.

As also shown, infusion pressure sensor 220 is attached to tubing (in-line) that will measure the blood flow pressure at the end of the system before it returns to the patient. Infusion Catheter 224 is positioned at a distal end of the system in order to return blood to the patient through a vein. At another terminal point, water vapor collection bag 222 will collect the condensed water vapor pulled from the blood by the WRT cartridge.

In the schematic of FIG. 24, blood is withdrawn from the body through withdrawal catheter 200 (an IV catheter inserted in the vein to withdraw blood out of the patient and into the system) using blood pump 204. Blood pump 204 can be provided in the form of a roller pump that pumps blood out of the patient while minimizing damage to red blood cells. The blood can be monitored by withdrawal pressure sensor 202 that allows for the measurement of blood flow out of the patient before reaching the blood pump. Discrete portions of the withdrawn blood are delivered via control valve 205 to the respective inlet ports of both ultrafiltration cartridge 206 and WRT cartridge 212, for ultrafiltration and water removal therapy, respectively. The amounts sent to each cartridge, in terms of both total amounts and in relative proportions of the whole, can be varied using the valve, depending on desired outcome. Additionally, some or all of the ultrafiltrate can be directed to the inlet port of the WRT cartridge 212 for further processing, in the manner described below.

The advantages of the approach shown in this schematic include: 1) it permits considerable flexibility in determining the proportions of blood that will be treated by UF as compared to WRT, 2) it permits highly efficacious treatment via the respective routes, 3) it permits blood to be delivered in a significantly higher flow rate to the WRT cartridge, and 4) it permits blood to be delivered at its normal viscosity to the WRT cartridge. By contrast, however, this approach typically requires increased blood priming volume.

In use, the withdrawal IV catheter 200 is placed in the vein. Once placed, the catheter is attached to the system's tubing set (to the end closest to the blood pump). The infusion IV catheter 224 can be placed at the same time into a separate vein in the patient and attached to the tubing at the opposite end of the system. Pressure sensors can be included in the circuit as desired, e.g., to monitor blood pressures flowing away from the patient and returned to the patient. Blood pump tubing is placed within the blood pump and connected to the first valve 205. The withdrawal blood pump 204 is turned on, to begin pumping the blood out of the patient and through the entire system. In FIG. 24, the valve 205 prior to the ultrafiltration and WRT cartridges can also be adjusted to allow the appropriate amount of blood flow to the lumens of both cartridges.

On the ultrafiltrate cartridge 206, tubing is connected to the side port 207, which is in fluid communication with the extraluminal space, and attached to the ultrafiltrate pump 209. The ultrafiltrate pump contains controls for the rate of ultrafiltrate removal from the cartridge. In turn, the tubing is connected to a valve 211 that allows control over the rate at which ultrafiltrate is delivered either as waste drainage into the ultrafiltrate collection bag 210, or permitted to continue on to the WRT cartridge 212. Ultrafiltrate that flows to the WRT cartridge can therefore be concentrated further, with water vapor removed and solutes returned to the blood stream. A pressure sensor 208 allows pressure monitoring of ultrafiltrate removal from the ultrafiltrate cartridge.

Another valve 221 is positioned just in front of (upstream from) the WRT cartridge 212 in order to permit control over the relative amounts of blood and ultrafiltrate that enter the hollow fibers 213 contained within the WRT. To create the WRT effect, one side port 217 of the WRT cartridge is connected with tubing to a dry air source 214 (for example, a hospital wall supply, a desiccant cartridge, or an air drier). Another side port 219 of the WRT cartridge is connected with tubing to a condenser 216 which, in turn, is connected to a vacuum source 218. The vacuum source pulls dry air through the cartridge housing, removing water vapor from blood via transmembrane conductance. The humidified air is delivered to a condenser 216, which in turn, delivers liquid water to the water vapor collection bag 222.

The condenser operates by circulating cool water through an internal coil that condenses the external water vapor into liquid water. The condenser delivers liquid water to the water vapor collection bag. From the backside of both cartridges, tubing is connected, optionally via a valve 203, in order to permit recombining of the filtered blood before it re-enters the patient. A sensor is optionally and preferably placed here to allow the user to know the pressure at which the blood is flowing back to the patient. The tubing after the valve is connected to the IV infusion catheter that returns the blood to the patient.

In the schematic of FIG. 25, a UF cartridge is used in series (here prior to) the use of a WRT cartridge. The blood components that are not removed from the ultrafiltration cartridge 206, therefore, are directed to the WRT cartridge 212 for water removal therapy. Water vapor is sent to the water vapor collection bag 222 while blood is delivered back to patient. In essence, the blood is subjected to ultrafiltration, with water removal therapy being performed on post-ultrafiltrate blood. This approach gives the highest combination of solute removal and solute concentration. On the other hand, blood will be of higher viscosity after passing through the ultrafiltration cartridge. Priming volume with two sequential cartridges will be increased.

The system of FIG. 25 is set up and operated in a manner analogous to that described with respect to FIG. 24. For instance, blood pump 204 can be used to adjust the appropriate amount of blood flow to the lumen of the fibers within the UF cartridge. Ultrafiltrate from the UF cartridge, in turn, is delivered using ultrafiltrate pump 209 that contains controls for the rate of ultrafiltrate removal. Ultrafiltrate waste would flow directly into a waste collection bag 210. There is no further concentration of the ultrafiltrate in this schematic, post-ultrafiltrate blood would then flow directly to the WRT cartridge. The system is also operated in a similar fashion as described with respect to FIG. 24, in terms of the manner in which WRT is performed.

Finally, in the schematic of FIG. 26, ultrafiltrate from the ultrafiltration cartridge 206 is delivered to the water removal therapy cartridge 212. Treated ultrafiltrate from the WRT cartridge 212 is delivered back to the patient along with blood from the ultrafiltration cartridge 206, again in a manner that permits both total and proportional amounts of each to be controlled. In essence, UF is performed on blood, with water removal therapy being performed on ultrafiltrate only. The advantages of this approach include: 1) reduced viscosity of ultrafiltrate compared to whole blood, and 2) reduced effect on hemoglobin levels of carbon dioxide and oxygen. On the other hand, this approach provides: 1) minimal effect on reduction of carbon dioxide and increased levels of oxygen if that affect is desired and 2) reduced flow rate of the ultrafiltrate through the WRT cartridge. Also, relatively high flow rates can often be required to prevent a drop in temperature, while low flow rates may require internal WRT cartridge heating.

With the withdrawal IV catheter 200 positioned, the blood pump 204 is used to adjust the appropriate amount of blood flow to the lumen of the ultrafiltration cartridge. On the ultrafiltrate cartridge 206, tubing is connected to the side port and attached to the ultrafiltration pump 209. The ultrafiltration pump contains controls for the rate of ultrafiltrate removal. The tubing is connected to a valve 211 that allows control over the rate of drainage into the ultrafiltrate collection bag 210 as waste or onto the WRT cartridge. Ultrafiltrate that flows to the WRT cartridge is concentrated further, (water vapor only pulled out, solutes returned to the blood stream).

To create the WRT effect one side port of the WRT cartridge is connected with tubing to a dry air source 214 (for example, a hospital wall supply, a desiccant cartridge, or an air drier). The other side port of the WRT cartridge is connected with tubing to a condenser 216 which, in turn, is connected to a vacuum source 218. The vacuum source pulls dry air through the cartridge housing, removing water vapor from blood via transmembrane conductance The humidified air is delivered to the condenser.

The condenser operates by circulating cool water through an internal coil that condenses external water vapor into liquid water. The condenser delivers liquid water to the water vapor collection bag 222. From the back side of the WRT cartridge, tubing is connected to a suitable connection (optionally including a valve) that permits recombining of the filtrate (from the WRT cartridge) and filtered blood (from the ultrafiltration cartridge) before it re-enters the patient. A sensor 223 is placed after the WRT cartridge to allow the measurement of the pressure at which the filtrate is flowing out of the WRT cartridge. Another sensor 220 is placed after the final valve to measure the pressure at which the blood is flowing back to the patient. The tubing after the valve is connected to the IV infusion catheter that returns the blood to the patient. Recirculation of Post WRT fluid to maintain high flow and temperature.

A limitation of performing WRT on ultrafiltrate is the flow of ultrafiltrate though the WRT cartridge is decreased compared to blood flow. One embodiment that will overcome this limitation is to recirculate a portion of the post-WRT fluid back into the WRT inlet. Optionally, the recirculated fluid can be heated prior to return to the WRT inlet.

Figure 22:
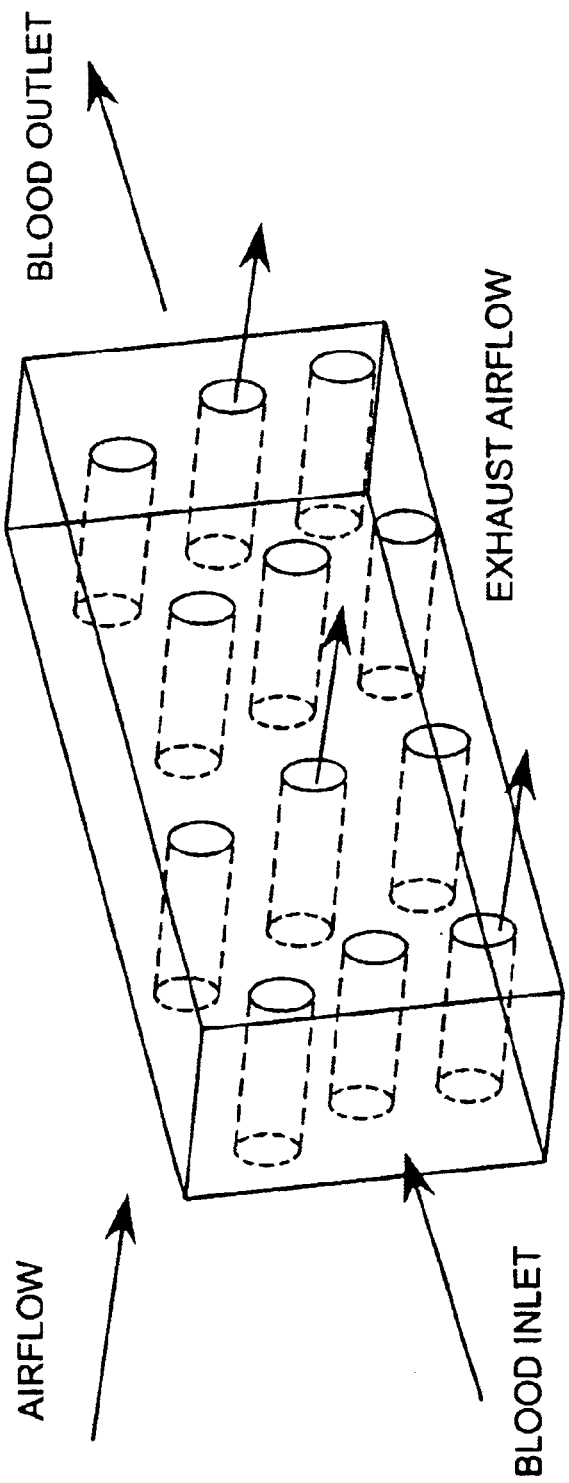
FIGS. 22 and 23 show optional design characteristics as described herein.

One embodiment that can provide improved efficacy is shown as FIG. 22, based on the premise that shorter fibers will typically be more efficient than long hollow fibers. Multiple short hollow fibers will produce the same surface area but at greater efficacy compared to fewer long fibers. Short, larger ID fibers also tend to reduce pressure drop along the length of the fiber, and therefore create a more uniform transmembrane pressure. Low magnitude, uniform transmembrane pressure may allow use of hydrophilic fibers without bulk flow of fluid into the lumen, or optionally, with increasing transmembrane pressure, ultrafiltration can be performed with the same cartridge.

Figure 23:
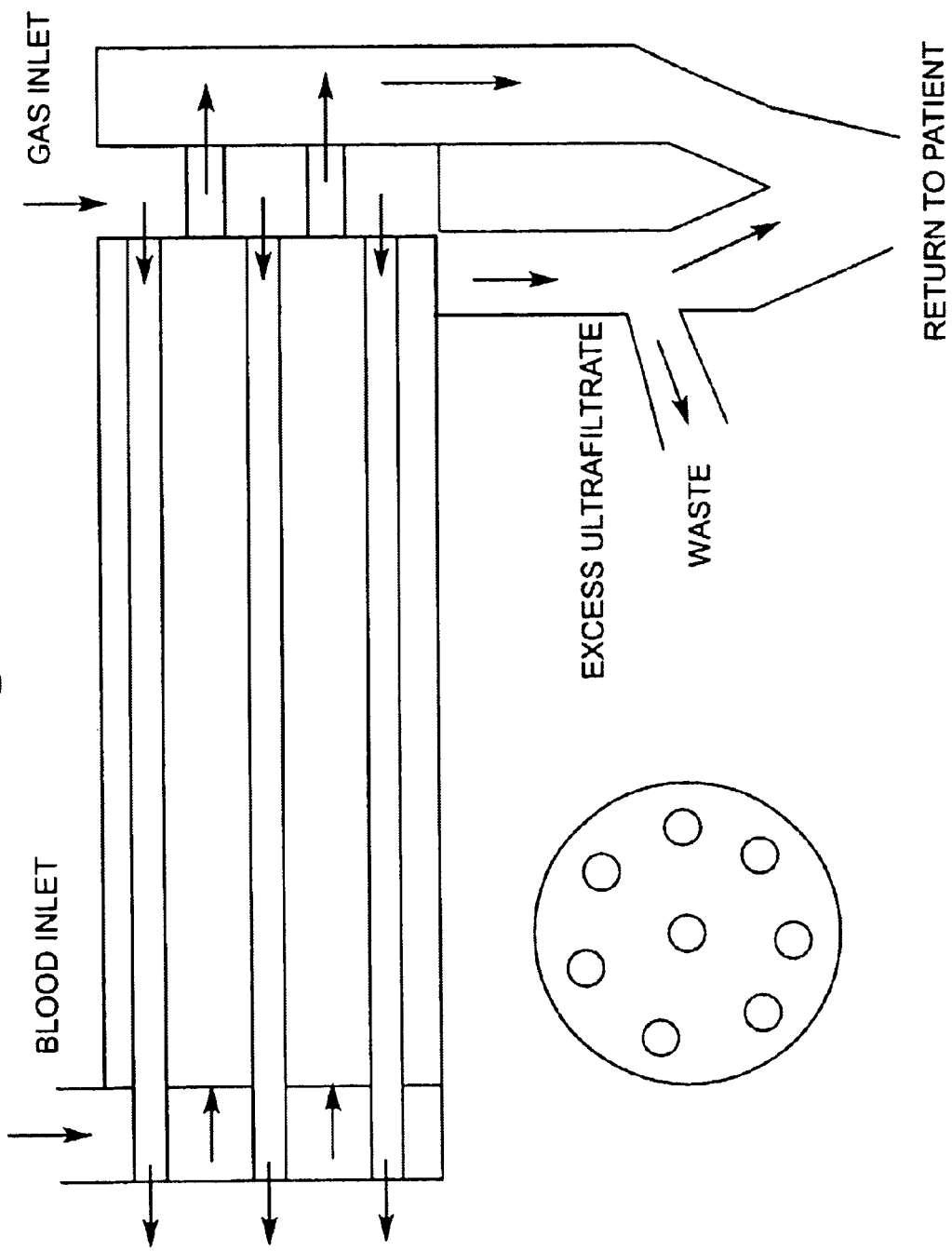

FIG. 23, by contrast, shows a diagram of the flow encountered using both WRT and UF fibers in the same cartridge, with WRT being performed on the ultrafiltrate within the cartridge.

EXAMPLE 1

Initial studies were performed to demonstrate that WRT removes water in the vapor phase and not in the liquid (bulk) phase.

Figure 27:
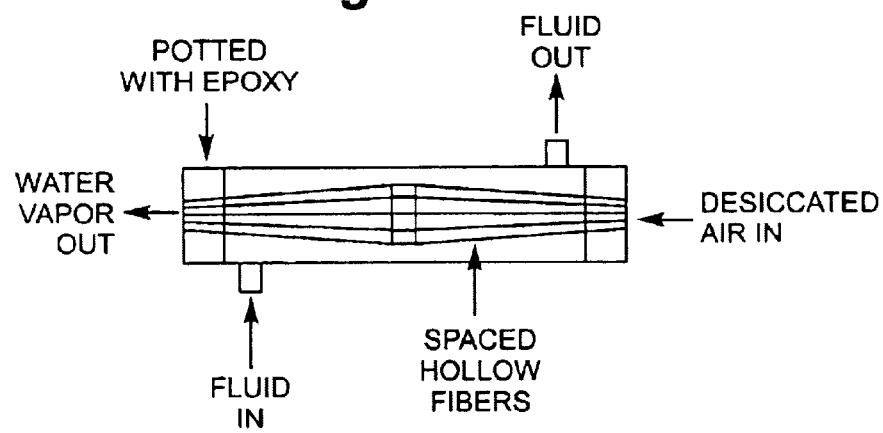
FIG. 27 shows a diagram of a cartridge of the type prepared and used in Example 1 below.

WRT cartridges were made by potting hollow fibers in plastic tubing, in the configuration shown in FIG. 27. The tube material was typically polycarbonate with nominal dimensions of 60 mm in length and 8 mm I.D. After potting, exposed length of fibers was 4.5–5 mm. Various numbers of fibers in any particular cartridge were examined. Side ports were attached to the tubing in order to allow either air or fluid flow along the outside of the fibers.

A fluid loop was attached to the side ports while desiccated air was passed through the hollow fiber lumens. Initial tests examined various fiber types/manufacturers and the ability to remove water vapor from an electrolyte solution in a flowing loop. After removing water vapor, the solution was examined for concentrated electrolytes (sodium, potassium and chloride). The electrolyte levels in the concentrated solution matched the values expected (for example, remove 10% of the water from the solution, the electrolytes were concentrated 10%). Various temperatures and flow rates of fluid and desiccated air were examined.

Two cartridges each containing 24 hollow polypropylene fibers (0.026 cm O.D. with exposed length of 4.5 cm) were examined. Desiccated room temperature air was passed through the hollow fiber bundle at 500 ml/min. Room temperature blood (sheep) was circulated through tube at 1 ml/min. After 80 minutes, 11% of the blood volume was removed. Electrolytes of the concentrated blood matched expected values.

In order to determine if hollow fibers may pass electrolytes (via bulk water) in addition to water vapor, a commercially available cartridge containing polypropylene fibers was used. Desiccated 37° C. air was passed through the hollow fiber bundle at 61 liters per minute. 37° C. blood (sheep) was circulated external to the fibers at 60 ml/min. Water vapor was collected and analyzed. Sodium, potassium and chloride were present at levels less than the detection limit of the instrumentation used (0.1, 0.02 and 0.15 meq, respectively).

Based on the results obtained above, it can be seen that removal of water vapor concentrates fluids, including blood, without loss of electrolytes from the fluid. Bulk water removal can be eliminated as a cause since there were no electrolytes observed in the collected fluid.

EXAMPLE 2

WRT and other methods can be used singly or in various combinations. Each combination will have specific affects on three independent parameters; 1) rate of solute flux, 2) effluent concentrations solutes, and 3) rate of water flux. These relationships can be quantified by mass balance formulas.

Two methods are currently used to treat fluid overload: ultrafiltration, and combination ultrafiltration and reinfusion of replacement fluid. Both result in a net removal of water. The combination treatment can accomplish net removal of water by removing more plasma (ultrafiltration) than is replaced with reinfused saline.

A comparison of WRT with UF, reinfusion, and combinations of UF and reinfusion are shown in the figure. Each data point on the line represents an increase in fluid transfer. Reinfusion alone results in an increase of sodium and plasma volume. A one to one combination of reinfusion and UF results also results in an increase in sodium, but no change in plasma volume. Neither of these conditions would have any benefit for treatment of CHF. Ultrafiltration alone will result in net sodium removal while removing up to 480 ml/hr of fluid. A 3:1 combination of UF and reinfusion will result in up to 480 ml/hr fluid loss and a reduction of total body sodium, but there is little improvement in serum sodium concentrations. WRT alone will remove 480 ml/hr of water, and increase sodium concentrations. Increased sodium concentrations will normalize the neurohumeral axis. Given these limitations of low plasma turnover, WRT is unique in its ability to concentrate sodium.

A combination of UF and reinfusion can result in net removal of fluid and normalization of the serum sodium concentrations, but at the cost of high plasma turnover.

Figure 30:
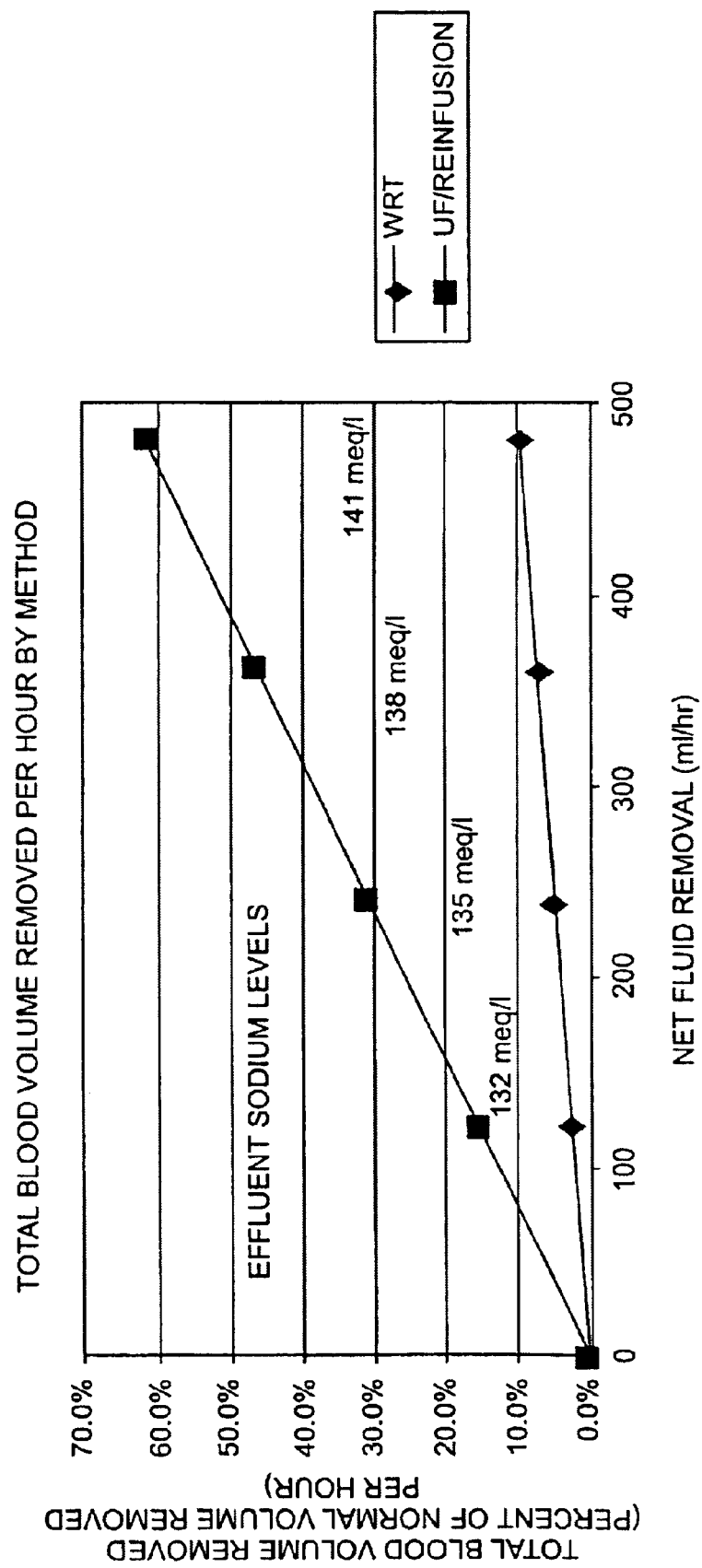
FIG. 30 is a graph showing total blood volume removed per hour.

The graph (FIG. 30) shows how much blood plasma must be removed (and replaced with normal saline) to concentrate sodium. The calculations are for starting serum levels of 130 meq/l. As the fluid removal rate is increased, the concentration of effluent increases, but 62% versus 9.6% blood volume has to be removed per hour for ultrafiltration and reinfusion versus WRT alone. Over 8 hours, that is 5× versus 0.8×, respectively. For UF-Reinfusion, that is 25 liters out and 21 liters reinfused (versus target 4 liters for WRT alone). In addition to serum sodium, all the other electrolytes and other materials would also have to be replaced.)

It can be seen that there is less difference between the two methods if less net fluid removal is required and if hypertonic saline is infused. Given complications of high plasma turnover, costs of replacement of species other than sodium, and ability to only remove water, WRT (alone or in combination with UF) offers advantages over UF and replacement.

Thus, WRT offers a unique advantage in removal of water and concentration of solute. In combination with UF, removal of solute can also be performed to advantage.

EXAMPLE 3

Efficacy of WRT can be confirmed with in vivo studies. These studies are designed to test water removal by extracoporeal WRT in normal, non-injured animals. Replacement fluids are provided to maintain fluid homeostasis.

Design Outline for Short-Term Study:
1. Induce general anesthesia.
2. Femoral artery and vein is cannulated.
3. Bladder is cannulated with suprapubic catheter.
4. Serum and urinary samples are taken.
5. Begin circulation.
6. After six hours, serum and urine samples are taken.
7. The animal is euthanized.

Design Outline for Long-Term Study:
1. Induce general anesthesia.
2. Femoral artery and vein is cannulated.
3. Bladder is cannulated with suprapubic catheter.
4. Serum and urinary samples is taken.
5. Begin extracorporeal circulation.
6. After six hours, serum and urine samples are taken and the animal is allowed to recover.
7. At twenty four hours the animal is anesthetized again, serum and urine samples taken again, and the animal then euthanized.

The study is performed with male Yorkshire/Hampshire pigs weighing 40 lbs (±5 lbs. Restrict the animals from food for twelve hours prior to surgery with water ad libitum. The pigs are pre-anesthetized with a mix of ketamine (100 mg/ml)/xylazine (100 mg/ml) at 10 cc/1.5 cc respectively at 0.15 cc per pound IM. In a surgical prep room the animals are shaved at the car and neck. Once transferred to the surgery room, the animal is placed on a heating pad to maintain 100.0–102.0 F.° core temperature, and connected to a Nellcor pulse-oximetry unit to monitor pulse and oxygen saturation. The carotid artery is cannulated for blood pressure measurement and blood sampling. The carotid line will be maintained post-anesthesia for blood sampling (Wilcox et al. 2000). The auricular vein is cannulated with a 22 gauge IV (Jelco, J&J Medical, Arlington, Tex.) catheter and connected to an intravenous minidrip set and bag of Lactated Ringers with 5% Dextrose solution (Baxter Health Corp, Deerfield, Ill.), at a rate of 2.7 drops per second (5–10 ml/kg/hour).

The animal is intubated with a 5 mm endotracheal tube, and given oxygen at 2 L/min, Isoflurane (3.0–2.0%) and Nitrous Oxide (½ rate of Oxygen) until a deep plane of anesthesia is reached. Vitals are recorded every 60 minutes including systemic pressure, oxygen saturation, temperature, pulse, and respirations. A baseline blood samples are taken through the arterial line.

Extracorporeal Circulation. The method of Kim et al. (2002) is utilized for extracorporeal circulation. After induction of general anesthesia and neck exposure, a two-lumen hemodialysis catheter (Arrowgard Blue catheter, 12 Fr, 20 cm, Arrow International, Reading Pa.) is placed into the jugular vein. The neck wound is stapled closed. Heparinized the animal with a bolus intravenous injection of 5000 Units. Primed the system tubing and pump with heparinized saline. The system is connected to the hemodialysis catheter. The blood pump is run at 100 ml/min. One-quarter normal saline is given to replace water loss. The goal is to maintain homeostasis. Water loss will be determined by on-site measurement of serum sodium. Water replacement will be adjusted accordingly. At the endpoint of 6 hours, the animal is in a deep plane of anesthesia (Isoflurane), and final blood and urine sample taken. For the six hour treatment animals, the pigs are euthanized immediately. For the twenty-four hour animals, then animals are allowed to recover and returned to the cage. Immediately before awakening, a one-time injection of Banamine (flunixin meglumide 2.2 mg/k) is given IM for pain relief. Food and water are given ad libitum. At twenty-four hours, the pig is re-anesthetized with the same ketamine/xylazine mix. Once the drug has taken affect, serum and urine samples are drawn, and then the pig is euthanized with 40 mEql of potassium chloride.

This study can demonstrate the ability of WRT to remove water from plasma. Possible compensatory mechanisms and regulation of respiratory gases can be studied in vivo.

What is claimed is:

1. A method of treating tissue swelling, the method comprising the step of employing one or more semipermeable membranes in combination with a hydratable medium in order to remove substantially only water through the semipermeable membrane(s) and from a biological fluid associated with the swelling, wherein the hydratable medium comprises a hydratable gas, and further comprising the use of one or more semipermeable membranes in order to perform ultrafiltration on the same or different biological fluid, in order to remove both water and permeable solutes from the biological fluid, and either in series or parallel with the water removal step.

2. A method according to claim 1 wherein the method is used to treat swelling associated with congestive heart failure, and provides a desired combination of ultrafiltration to remove water and permeable solutes, together with water removal therapy to remove substantially only water.

3. A method according to claim 2 wherein both ultrafiltration and water removal therapy are performed in an extracorporeal fashion.

4. A method according to claim 3 comprising respective extracorporeal cartridges in which both ultrafiltration and water removal are performed in parallel on different aliquots of blood.

5. A method according to claim 4 wherein the cartridges each comprise a plurality of hollow fibers together with extraluminal and intraluminal flow paths, the hydratable medium comprises a desiccated gas delivered to the intraluminal flow path, and the biological fluid comprises blood or ultrafiltrate delivered to the extraluminal flow path.

6. A method according to claim 5 wherein the fibers are formed of materials selected from the group consisting of polytetrafluoroethylene, polypropylene, polyvinylidene difluoride, acrilic copolymers, polyacrylonitrile, polyethersulfone, cellulose and polysulfone.

7. A method according to claim 4 wherein the cartridges each comprise a plurality of hollow fibers together with extraluminal and intraluminal flow paths, the hydratable medium comprises a desiccated gas delivered to the extraluminal flow path, and the biological fluid comprises blood or ultrafiltrate delivered to the intraluminal flow path.

8. A method according to claim 3 wherein the method is used to treat swelling associated with congestive heart failure, acute renal failure, chronic renal failure, hyponatremia, or water excess syndrome.

9. A method according to claim 3 further comprising the step of reinfusing the treated fluid with one or more components prior to return to the body.

10. A method according to claim 3 comprising respective extracorporeal cartridges in which both ultrafiltration and water removal are performed in series, with water removal therapy performed following ultrafiltration, and on at least a portion of the ultrafiltrate.

11. A method according to claim 1 wherein the method comprises an arteriovenous method based on a pressure differential between arterial and venous blood to drive blood through a water therapy removal cartridge.

12. A method of treating tissue swelling, the method comprising the step of employing one or more semipermeable membranes in combination with a hydratable medium in order to remove substantially only water through the semipermeable membrane(s) and from a biological fluid associated with the swelling wherein the method comprises a venovenous method based upon the pumping action of vaporization itself.

13. A method of treating tissue swelling, the method comprising the step of employing one or more semipermeable membranes in combination with a hydratable gas in order to remove substantially only water through the semipermeable membrane(s) and from a biological fluid associated with the swelling.

14. A method according to claim 13, further comprising the use of one or more semipermeable membranes in order to perform ultrafiltration on the same or different biological fluid, in order to remove both water and permeable solutes from the biological fluid, and either in series or parallel with the water removal step.

15. A method according to claim 14 wherein the tissue comprises the heart.

16. A method according to claim 15 wherein both ultrafiltration and water removal therapy are performed in an extracorporeal fashion.

17. A method according to claim 14 wherein the water removal and ultrafiltration are performed on the same biological fluid.

18. A method according to claim 13 wherein the semipermeable membranes are provided in the form of one or more cartridges that each comprise a plurality of hollow fibers together with extraluminal and intraluminal flow paths.

19. A method according to claim 18 wherein the hydratable gas is delivered to the intraluminal flow path, and the biological fluid is delivered to the extraluminal flow path.

20. A method according to claim 18 wherein the hydratable gas is delivered to the extraluminal flow path, and the biological fluid is delivered to the intraluminal flow path.

21. A method according to claim 13 wherein the one or more semipermeable membranes are provided in the form of hollow fibers.

22. A method according to claim 21 wherein the hollow fiber provides a permeability in the range of from about 1 kD to about 200 microns.

23. A method according to claim 22 wherein the permeability is between about 10 kD to about 10 microns.

24. A method according claim 23 wherein the permeability is between about 50 kD and about one micron.

25. A method according to claim 21 wherein the fibers are formed of materials selected from the group consisting of polytetrafluoroethylene, polypropylene, polyvinylidene difluoride, acrylic copolymers, polyacrylonitrile, polyethersulfone, cellulose and polysulfone.

26. A method according to claim 21 wherein the length of the fibers is between about 1 cm to about 100 cm.

27. A method according to claim 26 wherein the length is between about 5 cm and about 20 cm.

28. A method according to claim 21 wherein the fibers have an inner diameter (ID) of between about 50 microns to 5000 microns.

29. A method according to claim 28 wherein the inner diameter is between about 100 microns to about 1000 microns.

30. A method according to claim 13 further comprising the use of one or more monitoring components physically and/or functionally integrated with the placement and/or operation of the semipermeable membrane component.

31. A method according to claim 13 wherein the semipermeable membranes and hydratable gas are used in an extracorporeal fashion.

32. A method according to claim 31 wherein the semipermeable membranes are provided in the form of hollow fibers.

33. A method according to claim 32 wherein the hydratable gas is provided either within or surrounding the hollow fiber, in order to withdraw water vapor from biological fluid that is contacted with the opposite fiber surface.

34. A method according to claim 13 wherein the semipermeable membrane is employed in a position selected from the group consisting of: a) positioned directly within the tissue exhibiting swelling itself, b) positioned within a remote tissue having a indirect physiologic effect on the tissue exhibiting swelling, or c) positioned externally to the body itself in the form of a remote unit functionally connected to the body by a fluid flow circuit, and in turn to the swollen tissue site.

35. A method according to claim 13 wherein the hydratable gas is selected from dessicated or dehydrated air, carbon dioxide, nitrogen, and helium.

36. A method according to claim 13 wherein the flow of hydratable medium can be adjusted to in order to achieve water removal at any desired rate and and/or total amount.

37. A method according to claim 36 wherein flow of hydratable gas within the fibers is between about 1 l/mm to about 100 l/mm per 1000 $cm^2$ of fiber surface area.

38. A method according to claim 37 wherein the flow is between about 2 l/mm and about 25 l/mm per 1000 $cm^2$ of fiber surface area.

39. A method according to claim 36 wherein the water removal rate from the biological fluid is between about 100 ml/hr to about 500 ml/hr.

40. An apparatus for treating tissue swelling, comprising one or more semipermeable membranes in combination with a hydratable gas in order to remove substantially only water through the semipermeable membrane(s) and from a biological fluid associated with swelling in the heart.

41. An apparatus according to claim 40 wherein the one or more semipermeable membranes are in the form of hollow fibers.

42. An apparatus according to claim 41 wherein the fibers are formed of materials selected from the group consisting of polytetrafluoroethylene, polypropylene, polyvinylidene difluoride, acrylic copolymers, polyacrylonitrile, polyethersulfone, cellulose and polysulfone.

* * * * *